US008876765B2

(12) United States Patent
Mack et al.

(10) Patent No.: US 8,876,765 B2
(45) Date of Patent: Nov. 4, 2014

(54) PUMP MODULE FOR USE IN A MEDICAL FLUID DISPENSING SYSTEM

(75) Inventors: Stanley Paul Mack, Suwanee, GA (US);
Charles R. Patzer, Columbus, OH (US);
Stephen L. Vick, Norcross, GA (US)

(73) Assignee: Smiths Medical ASD, Inc., Keene, NH (US)

( * ) Notice: Subject to any disclaimer, the term of this patent is extended or adjusted under 35 U.S.C. 154(b) by 1575 days.

(21) Appl. No.: 11/749,265

(22) Filed: May 16, 2007

(65) Prior Publication Data

US 2008/0287887 A1  Nov. 20, 2008

(51) Int. Cl.
*A61M 37/00* (2006.01)
*A61M 5/142* (2006.01)
*A61M 5/14* (2006.01)
*A61M 5/168* (2006.01)
*A61M 5/38* (2006.01)

(52) U.S. Cl.
CPC ..... *A61M 5/1422* (2013.01); *A61M 2205/3355* (2013.01); *A61M 2205/3351* (2013.01); *A61M 2205/128* (2013.01); *A61M 5/16854* (2013.01); *A61M 5/385* (2013.01); *A61M 5/1413* (2013.01)
USPC ............................................. 604/131; 604/30

(58) Field of Classification Search
USPC ............... 604/30–34, 500, 65, 131, 151, 152, 604/156, 122
See application file for complete search history.

(56) References Cited

U.S. PATENT DOCUMENTS

| | | | |
|---|---|---|---|
| 2,311,851 A | 2/1943 | McClure | |
| 3,073,332 A | 1/1963 | Strader | |
| 4,065,230 A * | 12/1977 | Gezari | 417/317 |
| 4,084,606 A | 4/1978 | Mittleman | |
| 4,596,558 A | 6/1986 | Smith et al. | |
| 4,666,429 A | 5/1987 | Stone | |
| 4,819,684 A | 4/1989 | Zaugg et al. | |
| 4,838,860 A * | 6/1989 | Groshong et al. | 604/152 |
| 5,147,333 A | 9/1992 | Raines | |
| 5,176,658 A | 1/1993 | Ranford | |

(Continued)

FOREIGN PATENT DOCUMENTS

| | | |
|---|---|---|
| DE | 4336336 A1 | 5/1994 |
| EP | 0624379 A1 | 5/1994 |

(Continued)

OTHER PUBLICATIONS

Official Action issued in counterpart Japanese Application No. 2010-508576, dated Aug. 28, 2012, in Japanese language along with an English translation (6 pages).

*Primary Examiner* — Kevin C Sirmons
*Assistant Examiner* — Phillip Gray
(74) *Attorney, Agent, or Firm* — Wood, Herron & Evans, LLP

(57) ABSTRACT

A pump module for use in a medical fluid dispensing system is provided that includes a pump body and first and second pump chambers formed in the pump body. The module further includes a pair of chamber inlets and chamber outlets formed in the pump body, each associated with one of the pump chambers. Each of the pump chambers further includes a first portion having a generally spherical segment shape and a second portion integral with the first portion and having a generally conical shape, with the first and second portions in fluid communication with the chamber inlet and the chamber outlet. The second, conically shaped portion converges to the chamber outlet.

62 Claims, 12 Drawing Sheets

(56) References Cited

U.S. PATENT DOCUMENTS

| | | | |
|---|---|---|---|
| 5,385,540 A * | 1/1995 | Abbott et al. | 604/6.13 |
| 5,573,515 A | 11/1996 | Wilson et al. | |
| 5,609,572 A | 3/1997 | Lang | |
| 5,800,397 A | 9/1998 | Wilson et al. | |
| 5,882,343 A | 3/1999 | Wilson et al. | |
| 6,059,747 A | 5/2000 | Bruggeman et al. | |
| 6,099,511 A | 8/2000 | Devos et al. | |
| 6,176,903 B1 | 1/2001 | Wamsiedler | |
| 6,221,045 B1 | 4/2001 | Duchon et al. | |
| 6,344,030 B1 | 2/2002 | Duchon et al. | |
| 6,626,862 B1 | 9/2003 | Duchon et al. | |
| 6,656,157 B1 | 12/2003 | Duchon et al. | |
| 6,726,656 B2 * | 4/2004 | Kamen et al. | 604/131 |
| 6,866,654 B2 | 3/2005 | Callan et al. | |
| 2002/0183616 A1 | 12/2002 | Toews et al. | |
| 2004/0019313 A1 * | 1/2004 | Childers et al. | 604/5.01 |
| 2004/0143212 A1 | 7/2004 | Trombley et al. | |
| 2005/0096627 A1 | 5/2005 | Howard | |
| 2006/0049209 A1 * | 3/2006 | Baker | 222/252 |
| 2007/0134101 A1 * | 6/2007 | Jones et al. | 417/44.1 |
| 2009/0053086 A1 * | 2/2009 | Navarro | 417/493 |

FOREIGN PATENT DOCUMENTS

| | | |
|---|---|---|
| JP | 07503396 | 4/1995 |
| JP | H10080602 | 3/1998 |
| JP | 2000167040 A | 6/2000 |
| JP | 2001505106 A | 4/2001 |
| WO | 97/02852 | 1/1997 |
| WO | 9822167 A1 | 5/1998 |
| WO | 0136026 | 5/2001 |
| WO | 0158506 | 8/2001 |

* cited by examiner

PUMP MODULE FOR USE IN A MEDICAL FLUID DISPENSING SYSTEM

FIELD

The present invention relates generally to pumps, and more particularly to pump modules for use in medical fluid dispensing systems.

BACKGROUND

A variety of known pumps are used to dispense medical fluids. Syringes are widely used to dispense relatively small volumes of medical fluids, which can include highly concentrated medication. The maximum volume of syringes is typically about 60 ml. After this volume is dispensed, a caregiver must replace the depleted syringe to continue medication. Accordingly, syringes do not lend themselves to large volume applications such as the dispensing of large volumes of blood in various circumstances or the dispensing of high volumes of fluid, such as saline, to burn patients for example.

Syringes can be used in conjunction with syringe pumps that automatically operate the single plunger or piston of the syringe. Typically, the plunger tip is made of a soft, compliant rubber. When the plunger is pushed to dispense fluid, the tip is compressed and forced to the outer wall of the syringe. "Stiction" can then occur when the piston is moved again after being stationary, where "stiction" is a term known in the art derived from the ability to stick in combination with static and dynamic friction. In such an intermittent operation, the force required to overcome the "stiction" and start the piston moving can cause a bolus of fluid to be dispensed initially, which is undesirable.

Known pumps that are used in systems to dispense large volumes of medical fluids include peristaltic pumps, various diaphragm pumps, and single piston pumps. Although each type has been successfully used, they are subject to certain design and/or application challenges. For example, since the fluid flow passage in peristaltic pumps is normally open, fluid can be inadvertently supplied to the patient. This can occur if the tubing leading from a source of fluid, such as an IV bag, to the inlet portion of the pump is not clamped. Also, the continuous compression of the tubing defining the normally open flow path can result in tube fatigue, thereby necessitating replacement of the tube that adds to the operational cost of the system.

Peristaltic pumps are also affected by the hydraulic head height, resulting from the position of the source of fluid above the pump, which can result in further inaccuracies with the flow rate of the pump.

Large volume single piston pumps are known but do not exhibit fluid flow constancy. This is because a "dead time" occurs, for each pumping cycle, after the piston pumps a predetermined volume of fluid and then the output valve is closed, the piston is retracted and the piston chamber is refilled with fluid. This lack of flow constancy is undesirable since the half-life of certain medications can be on the order of seconds. If the medical fluid isn't delivered to and absorbed by the patient within this time, the medical fluid may be ineffective for its intended use. Flow constancy is a particularly important consideration when high potency medical fluids are being dispensed.

Known diaphragm pumps used in large volume medical fluid dispensing systems include those having a single elastomeric diaphragm and an associated piston to deform the diaphragm and dispense the medical fluid. Diaphragm pumps of this type can also include elastomeric check valves that communicate with the pump inlet and outlet ports. The compliant nature of these check valves can lead to variations in the breaking pressure of the valves, i.e., the pressures required to open or close the valves, which in turn can result in flowrate accuracy issues. A lack in flow constancy due to fluctuations in flowrate of the medical fluid being delivered is undesirable for the same reasons discussed previously with respect to the lack of flow constancy caused by "dead time." Another challenge associated with pumps having elastomeric diaphragms, is that the diaphragm(s) deform during the fill cycle and store potential energy. This energy is released during the pumping cycle, which can cause a bolus of fluid to be dispensed initially. This temporary spike in fluid flowrate also adversely affects flow constancy and is therefore undesirable.

Another known diaphragm pump used to dispense large volumes of medical fluids includes two elastomeric diaphragms that are pumped in alternating fashion. This pump does not include elastomeric check valves and the associated challenges. However, as with the single piston diaphragm pump, the compliant, elastomeric diaphragms are pressurized during the fluid fill cycle causing them to deform and store energy. Accordingly, when the corresponding output valve is opened at the beginning of a pumping cycle, a bolus of fluid can be dispensed, even without the associated piston moving, which is undesirable.

Another challenge associated with known large volume medical fluid pumps in general is the susceptibility to air bubbles forming in the fluid system and the typical requirement of caregiver intervention to "prime" the pump to eliminate the undesirable air bubbles. Air bubbles can be formed in the fluid delivery systems associated with the pumps due to pump cavitation or "outgassing" that can occur when the temperature of the fluid is raised. Once air bubbles are detected in the delivery system the pump typically shuts down and triggers an alarm advising a caregiver of a problem. The time it takes for the caregiver to remedy the problem results in an interruption in the delivery of medical fluid to the patient. Spurious alarms result in a waste of caregiver time as well as an interruption in fluid delivery to the patient.

Yet another challenge associated with medical fluid pumps is the requirement to replace the portion of the pump that is exposed to the fluid after a predetermined, relatively short period of time as a result of hospital procedures associated with infection control. This replacement must be accomplished in an expeditious and cost effective manner.

It is therefore desirable to provide a pump having a replaceable pump module for use in medical fluid dispensing systems, which can be used in small and large volume fluid applications and overcomes the disadvantages associated with known pumps used in medical fluid dispensing systems.

SUMMARY

In view of the foregoing and by virtue of the present invention, a pump module is provided for use in a medical fluid dispensing system comprising a pump body and first and second pump chambers formed in the pump body. A pair of chamber inlets and chamber outlets are formed in the pump body, each being associated with one of the pump chambers. Each pump chamber comprises a first portion having a generally spherical segment shape and a second portion integral with the first portion and having a generally conical shape. The first and second portions are in fluid communication with the chamber inlet and the chamber outlet. The second, conically shaped portion converges to the chamber outlet.

In other embodiments, the pump module can comprise one or more of the following features. The pump body can be made of a non-compliant material. The pump module can also include a fluid flow network formed in the pump body and operable for supplying fluid from a source of fluid to the pump chambers and for dispensing fluid from the pump chambers out of the pump body during operation of the pump. The pump module can also include a first fluid displacement member mechanically coupled to the pump body and operably extendable into the first pump chamber, wherein fluid is displaced out of the first pump chamber into the fluid flow network, and a second fluid displacement member mechanically coupled to the pump body and operably extendable into the second pump chamber, wherein fluid is displaced out of the second pump chamber into the fluid flow network.

The fluid flow network can include a plurality of non-displacement valves. Each of the non-displacement valves can be a rotatable valve having a stem, a coupling portion integral with the stem and a flow passage. The flow passage of each of the valves can extend substantially straight and transversely through the stem and the coupling portion can be adapted to be coupled to a rotational actuator. One of the non-displacement valves can be a three position input valve and the remaining two valves can be first and second output valves.

The pump module further includes an inlet port and an outlet port. The fluid flow network can further comprise first and second fluid supply passages, with the first fluid supply passage being in fluid communication with the inlet port and the first pump chamber when the input valve is in a first position. The second fluid supply passage can be in fluid communication with the inlet port and the second pump chamber when the input valve is in a second position and the first and second pump chambers can be fluidicly uncoupled with the inlet port when the input valve is in a third position.

A pair of porous air filters can be provided, each being selectively in fluid communication with one of the pump chambers. The outlet port is in fluid communication with the first pump chamber when the first output valve is in a first position; the first pump chamber is in fluid communication with one of the filters when the first output valve is in a second position; and the first pump chamber and the outlet port are fluidicly uncoupled when the first output valve is in a third position. Similarly, the outlet port is in fluid communication with the second pump chamber when the second output valve is in a first position; the second pump chamber is in fluid communication with the other filter when the second output valve is in a second position; and the second pump chamber and the outlet port are fluidicly uncoupled when the second output valve is in a third position.

The module can further comprise first and second pressure sensors, each in fluid communication with one of the pump chambers. Each air filter is operably effective for removing air entrained within a fluid supplied to the filter and for discharging the air out of an air vent. Each filter can include a hydrophobic medium and each filter can be a Gortex® air filter.

According to a second aspect of the present invention, a method of manufacturing a pump module for use in a medical fluid dispensing system is provided comprising using a plastic material to make a pump body of the module, forming first and second pump chambers in the pump body, and forming a fluid flow network in the pump body, wherein the fluid flow network communicates with the pump chambers.

The method can further comprise forming each of the first and second pump chambers to comprise a first portion having a generally spherical segment shape and a second portion integral with the first portion and having a generally conical shape. The step of forming can comprise injection molding the first and second pump chambers.

According to a third aspect of the present invention, a pump is provided for use in a medical fluid dispensing system comprising a pump body made of a non-compliant material and first and second pump chambers formed in the body. The pump further comprises a fluid flow network formed in the pump body and operable for supplying fluid from a source of fluid to the pump chambers, and for dispensing fluid from the pump chambers out of the pump body during operation of the pump. The pump further comprises first and second fluid displacement devices, each mechanically coupled to the body and operably extendable into the corresponding one of the pump chambers, wherein fluid is displaced out of the pump chambers. The first and second fluid displacement devices are operable independently from one another.

In other embodiments, the pump can further comprise one or more of the features of the pump module of the present invention discussed previously.

According to a fourth aspect of the present invention, a method for pumping fluid in a medical fluid dispensing system is provided comprising the steps of providing a pump comprising a pump body made of a non-compliant material, first and second pump chambers formed in the pump body, with the pump further including a fluid flow network formed in the body. The method further comprises supplying fluid through the fluid flow network to the pump chambers and independently pumping at least a portion of the fluid out of each of the pump chambers, through the fluid flow network and out of the pump.

The method can further comprise initiating a first pumping cycle to pump at least a portion of the fluid out of the first pump chamber and initiating a second pumping cycle, before the first pumping cycle is completed, to pump at least a portion of the fluid out of the second pump chamber.

The method can further comprise refilling the first pump chamber after the completion of the first pumping cycle and during the second pumping cycle, and testing for the presence of air within the first pump chamber after the completion of the refilling cycle.

DRAWINGS

These and other features, aspects and advantages of the present invention will become better understood with regard to the following description, appended claims and accompanying drawings wherein:

DESCRIPTION

Figure 1:
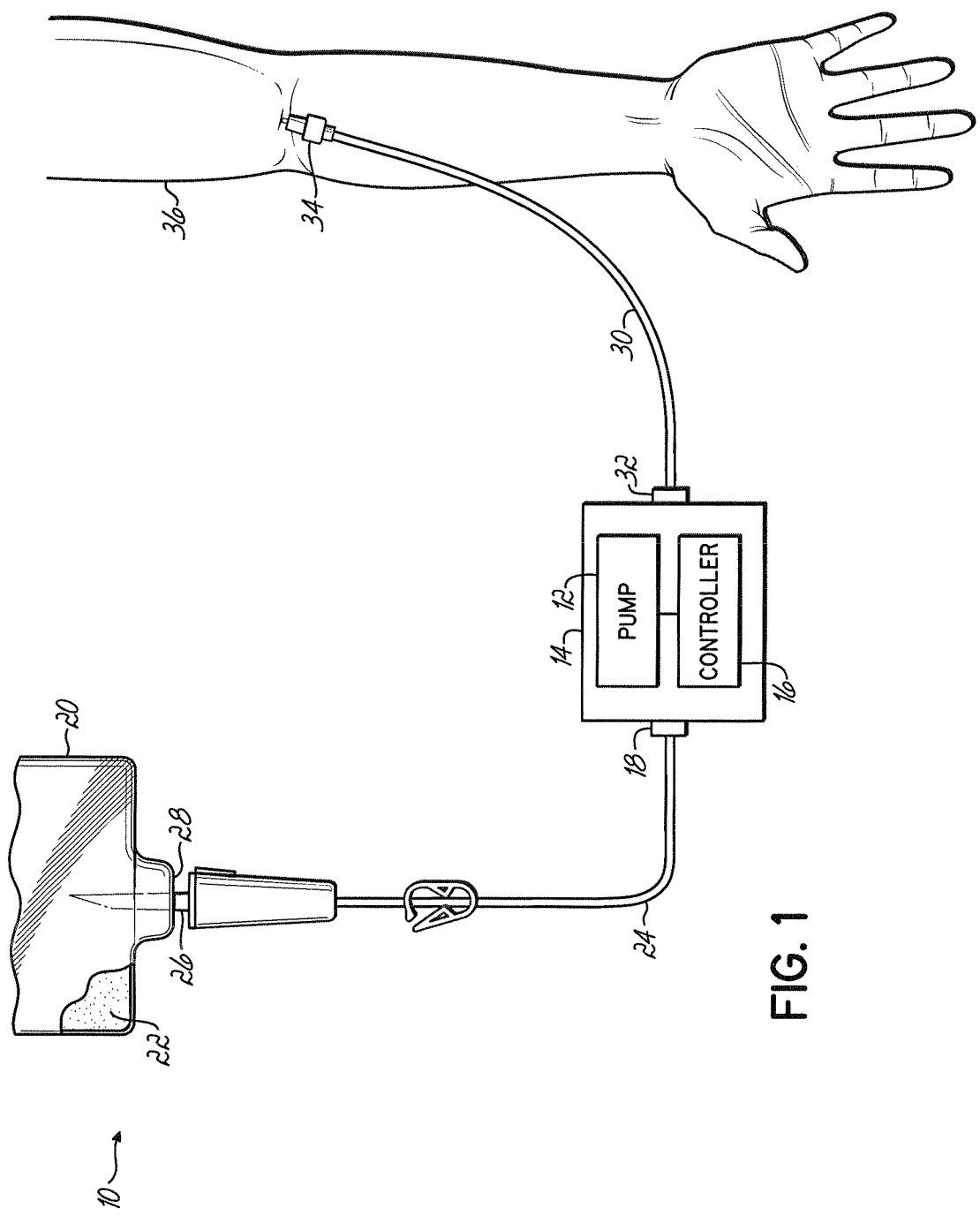
FIG. 1 is a schematic illustration of a system for dispensing medical fluids intravenously to a patient, which incorporates a pump according to the principles of the present invention.

Referring now to the drawings, FIG. 1 illustrates a system 10 for dispensing medical fluids intravenously to a patient, with system 10 incorporating a pump, indicated schematically at 12, in accordance with the principles of the present invention. Pump 12 can be disposed within an enclosure, illustrated schematically at 14, and can be electrically coupled to a controller 16 that can also be disposed within the enclosure 14, and that can control the operation of pump 12.

An fluid inlet (not shown in FIG. 1) of pump 12 is fluidicly coupled to a source of fluid to be dispensed which can comprise a bag 20, commonly referred to as an IV bag, containing a fluid 22 therein. The fluid 22 can comprise a variety of medications and can also include other fluids, such as saline solution, as known in the art. The system 10 further includes a first section of tubing 24 that can comprise a single piece of tubing or multiple pieces of interconnected tubing. Tubing 24 can pass through a tubing inlet 18 of enclosure 14, and be fluidicly coupled to a fluid inlet (not shown in FIG. 1) of pump 12 by one or more conduits and fluid connectors (not shown). The opposite end of tubing 24 can terminate in a spike 26 adapted to pierce a port 28 of the IV bag 20.

System 10 also includes a second section of tubing 30 that can comprise a single piece of tubing or multiple pieces of interconnected tubing. Tubing 30 can pass through a tubing outlet 32 of enclosure 14, and be fluidicly to a fluid outlet (not shown in FIG. 1) of pump 12 by one or more conduits and fluid connectors (not shown). The opposite end of tubing 30 can terminate in a catheter 34 inserted intravenously into an arm 36 of a patient.

Figure 2:
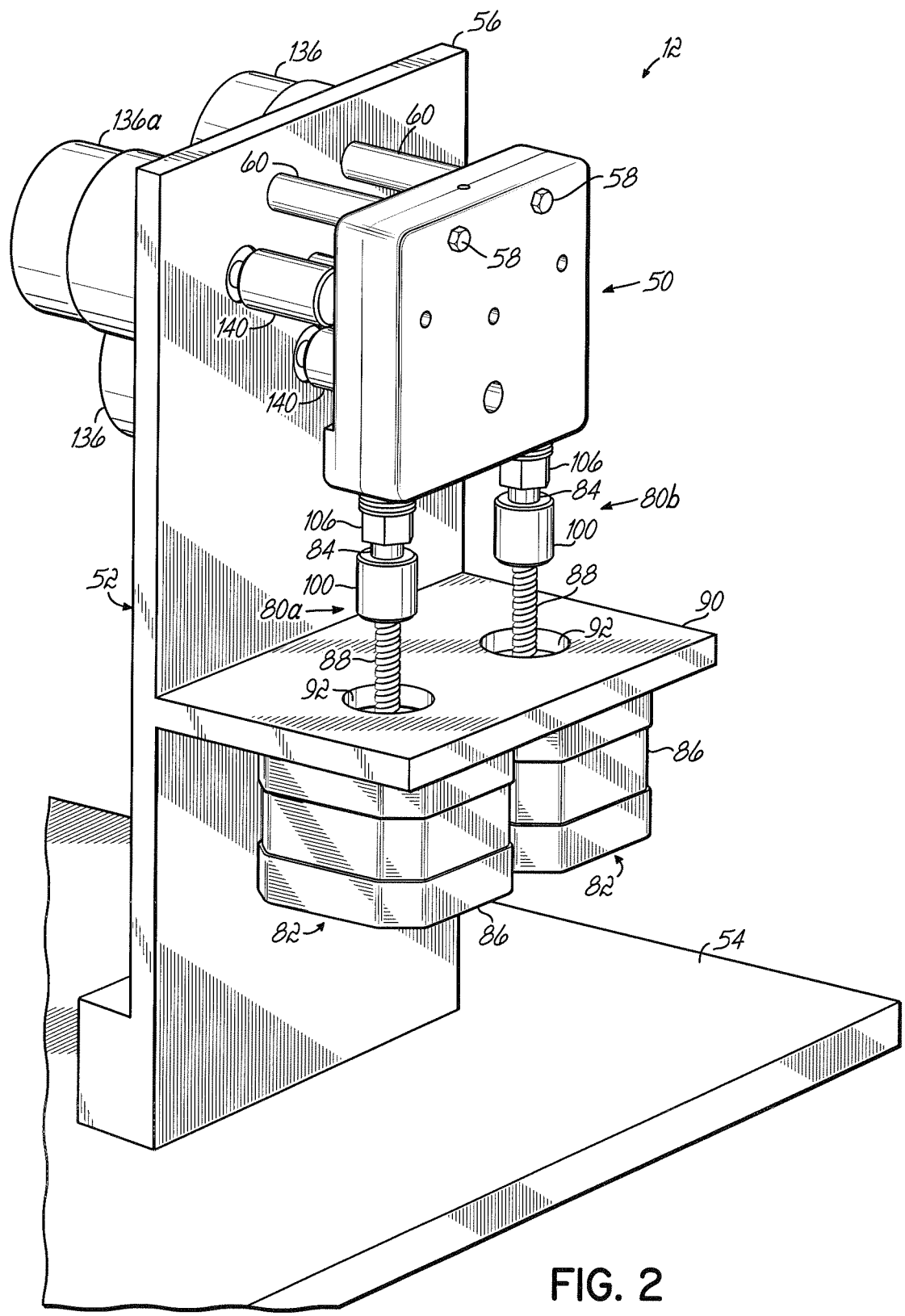
FIG. 2 is a perspective view of the pump shown schematically in FIG. 1.
Figure 3A:
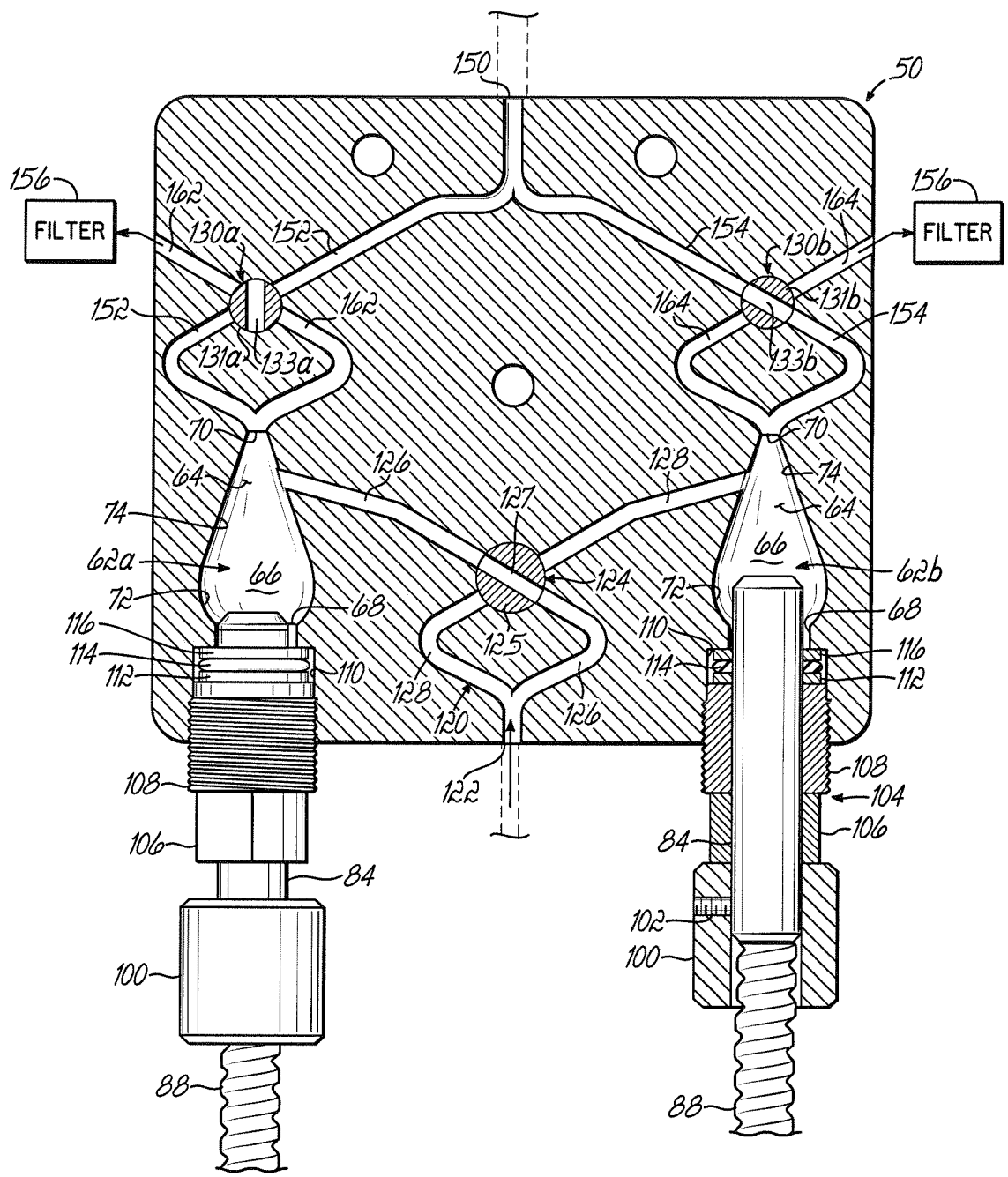
FIGS. 3A-3H are a series of front elevation views of a portion of the pump shown schematically in FIG. 2 illustrating the positions of the pump input valve and the two pump output valves during various phases of operation of the pump.
Figure 3B:
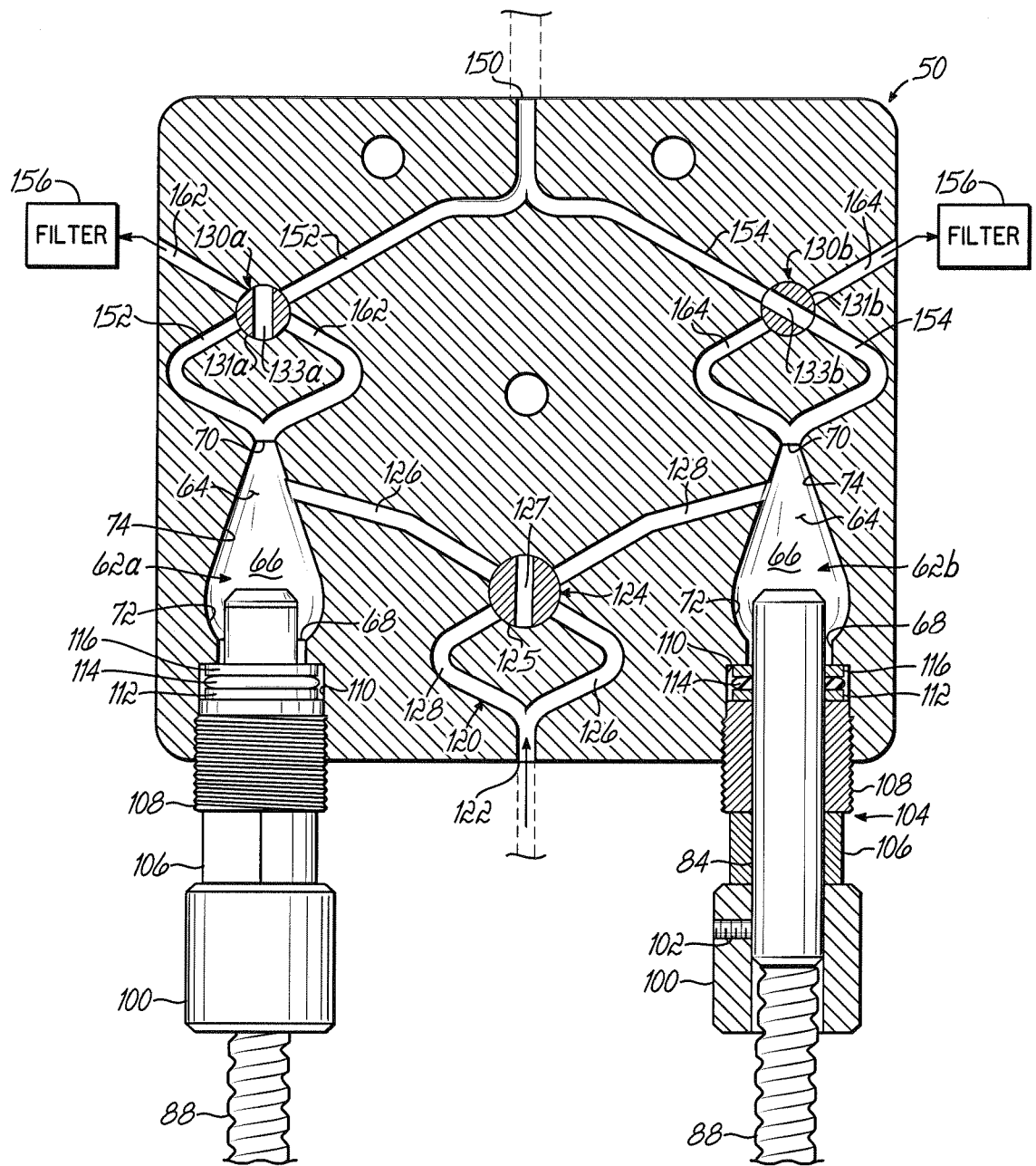
Figure 3C:
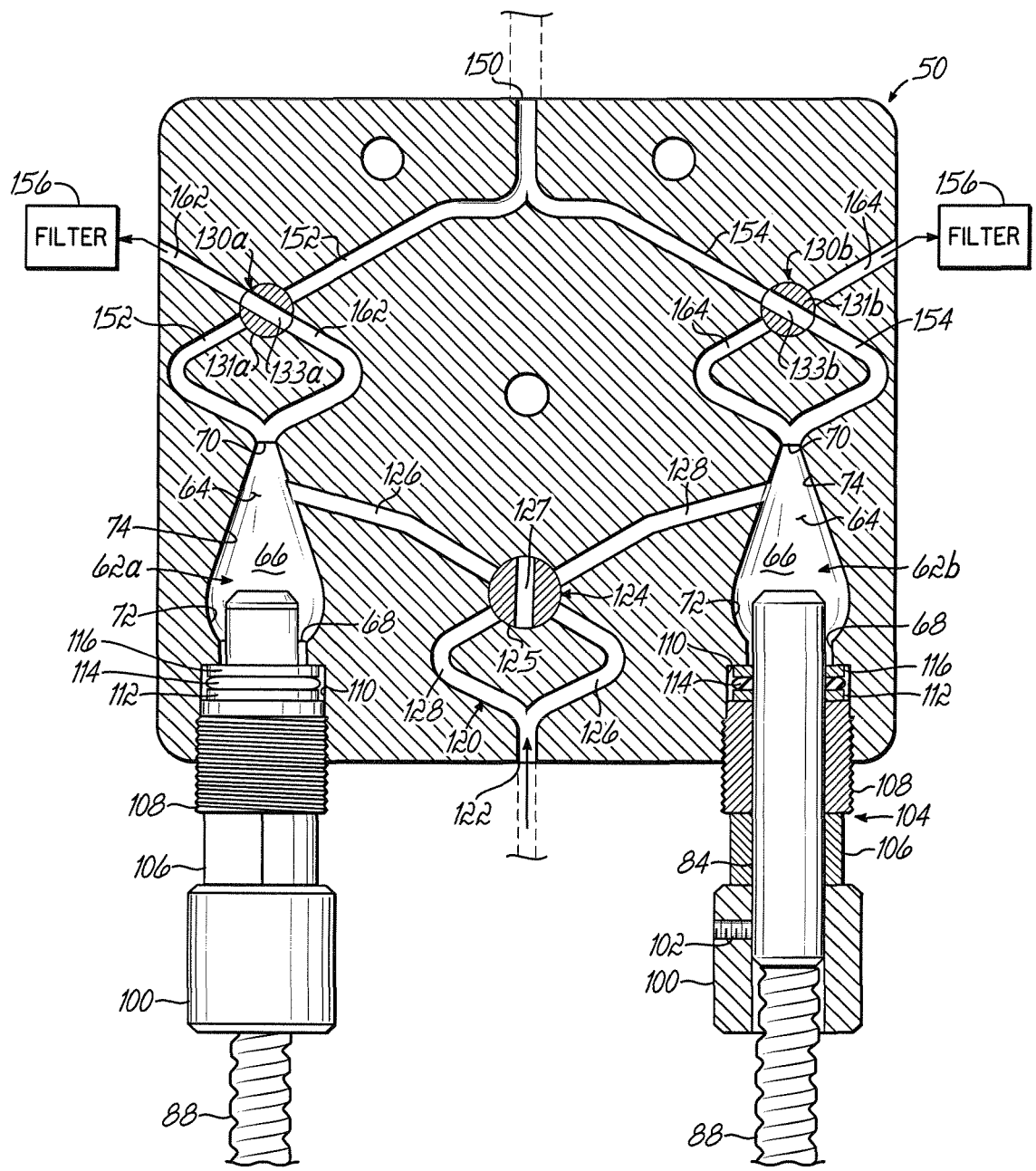
Figure 3D:
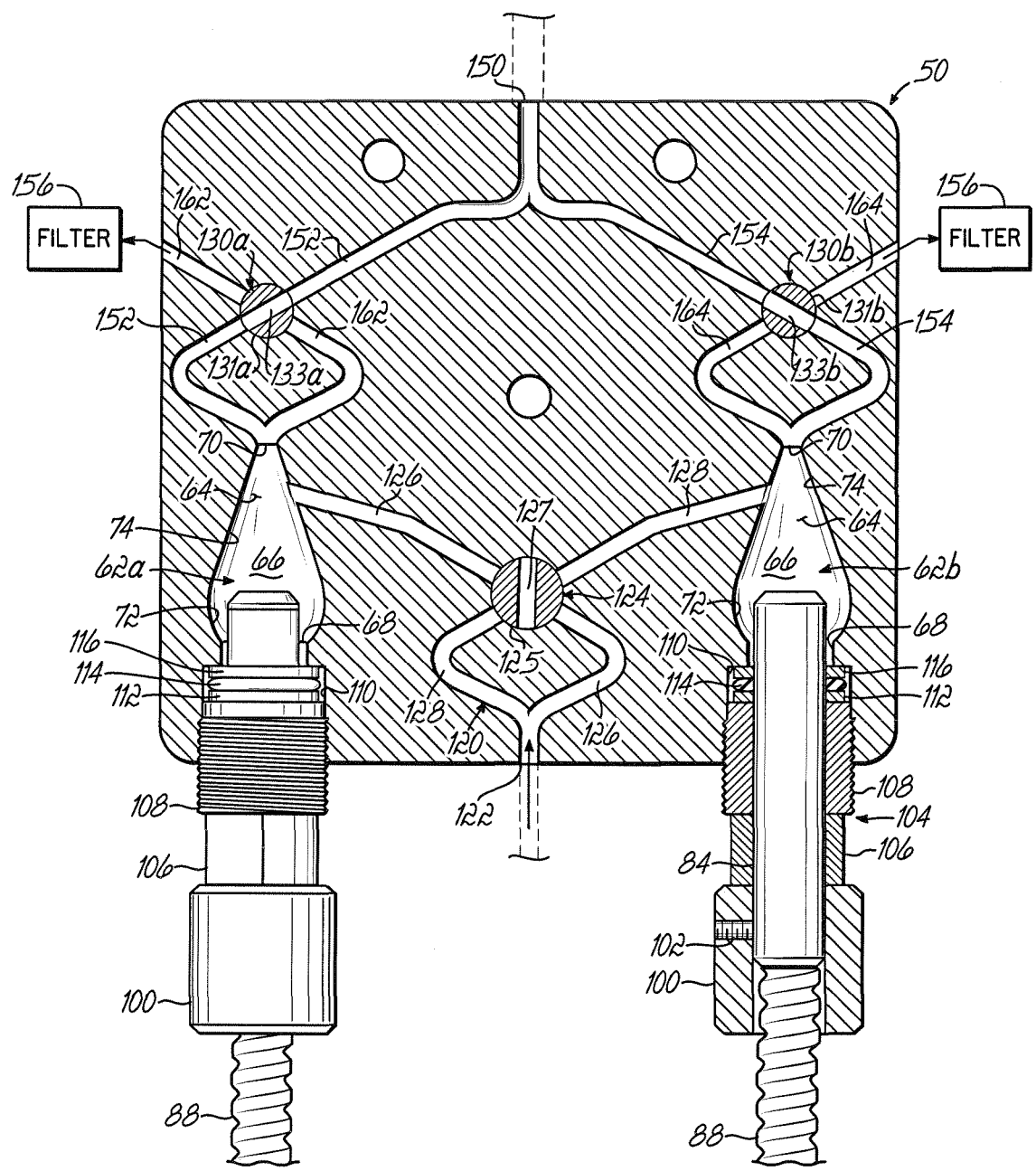
Figure 3E:
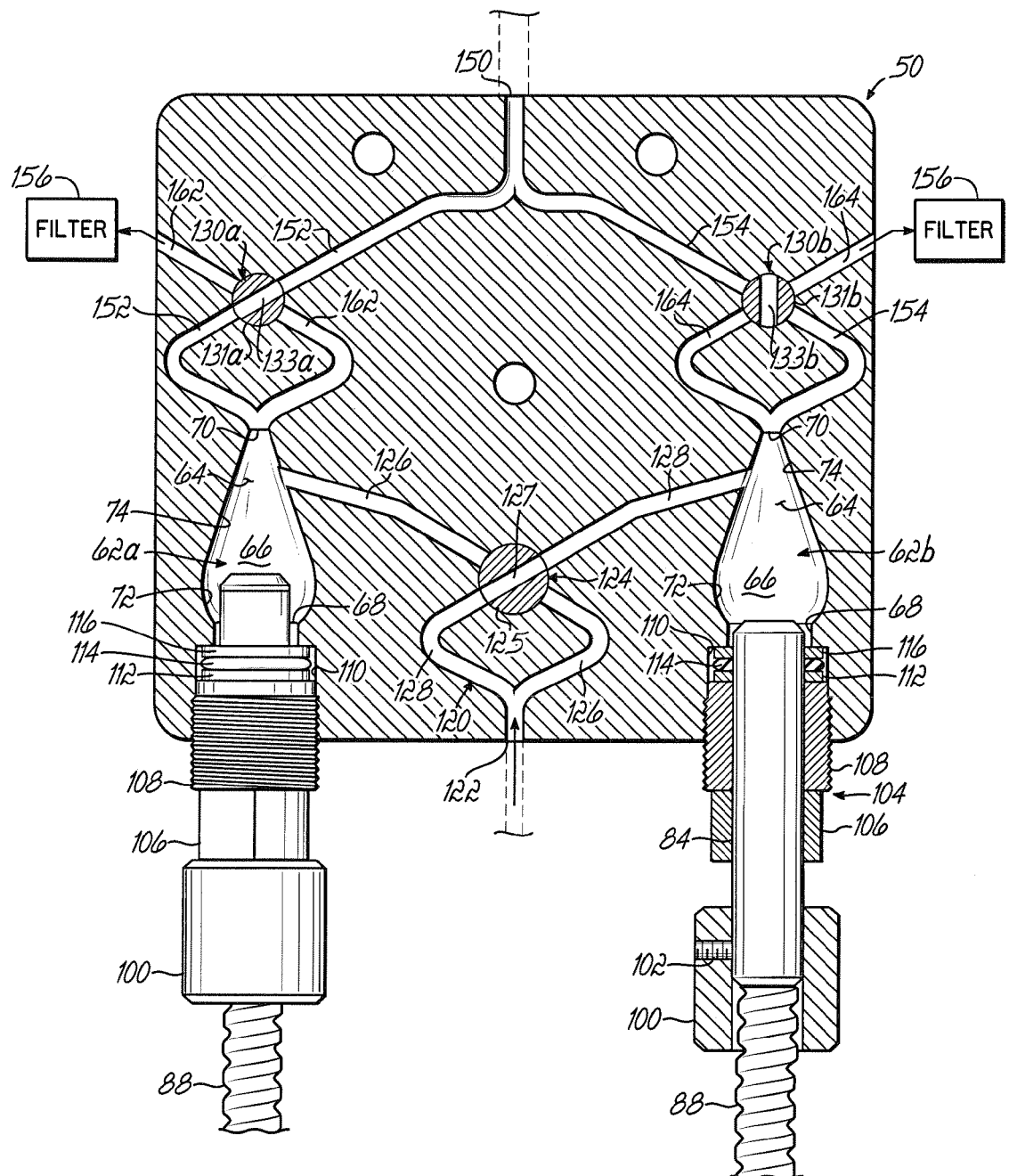
Figure 3F:
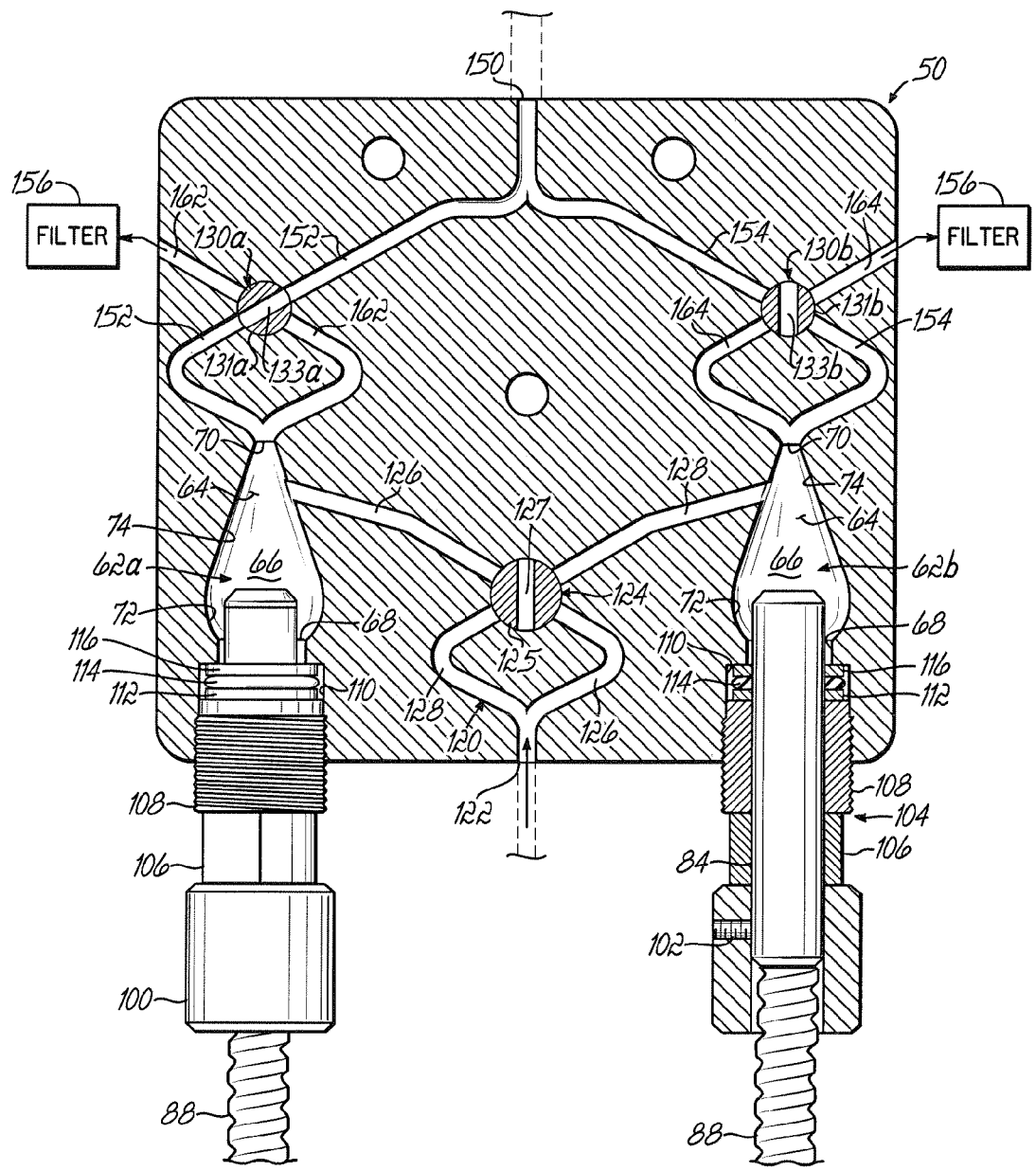
Figure 3G:
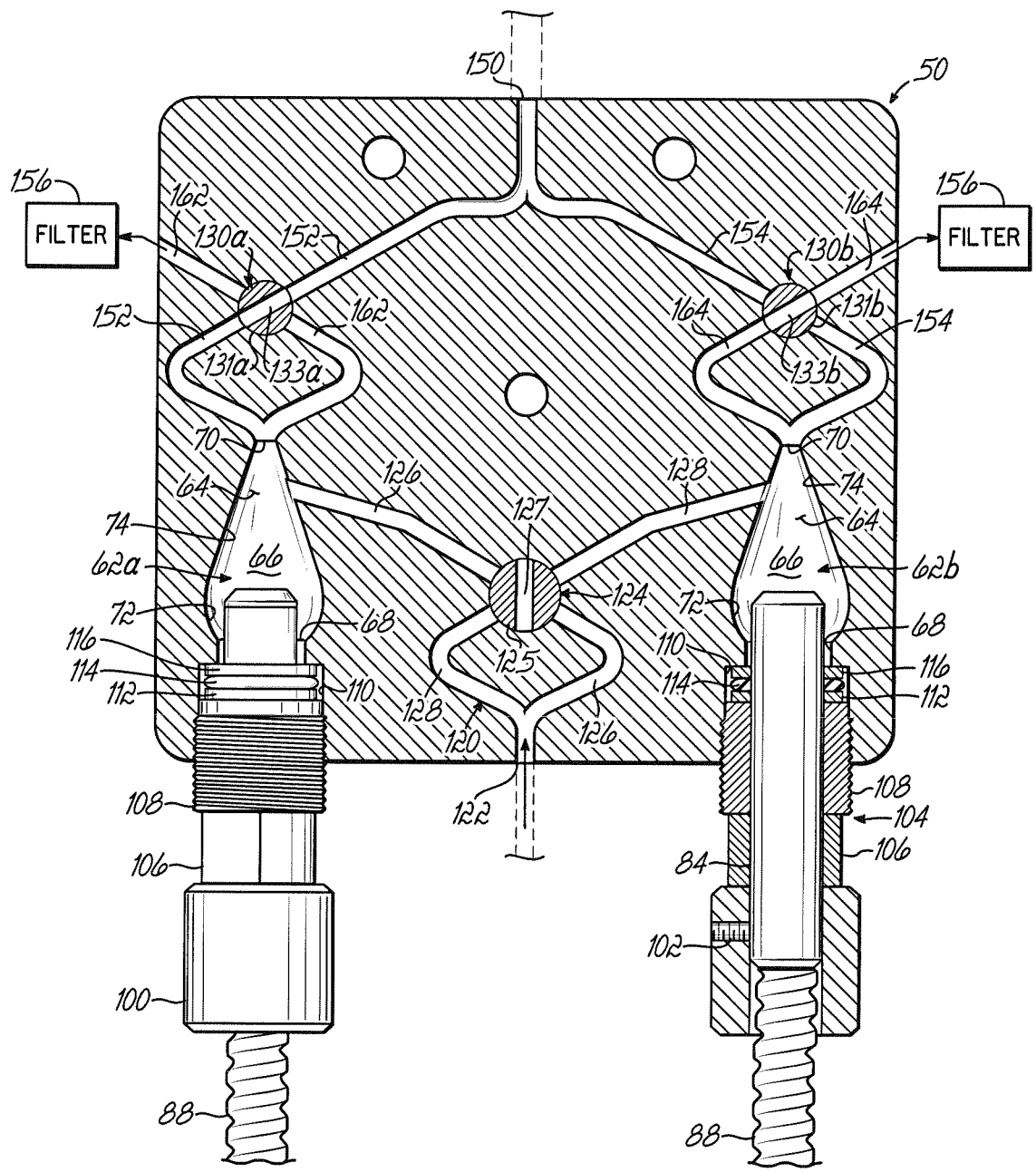
Figure 3H:
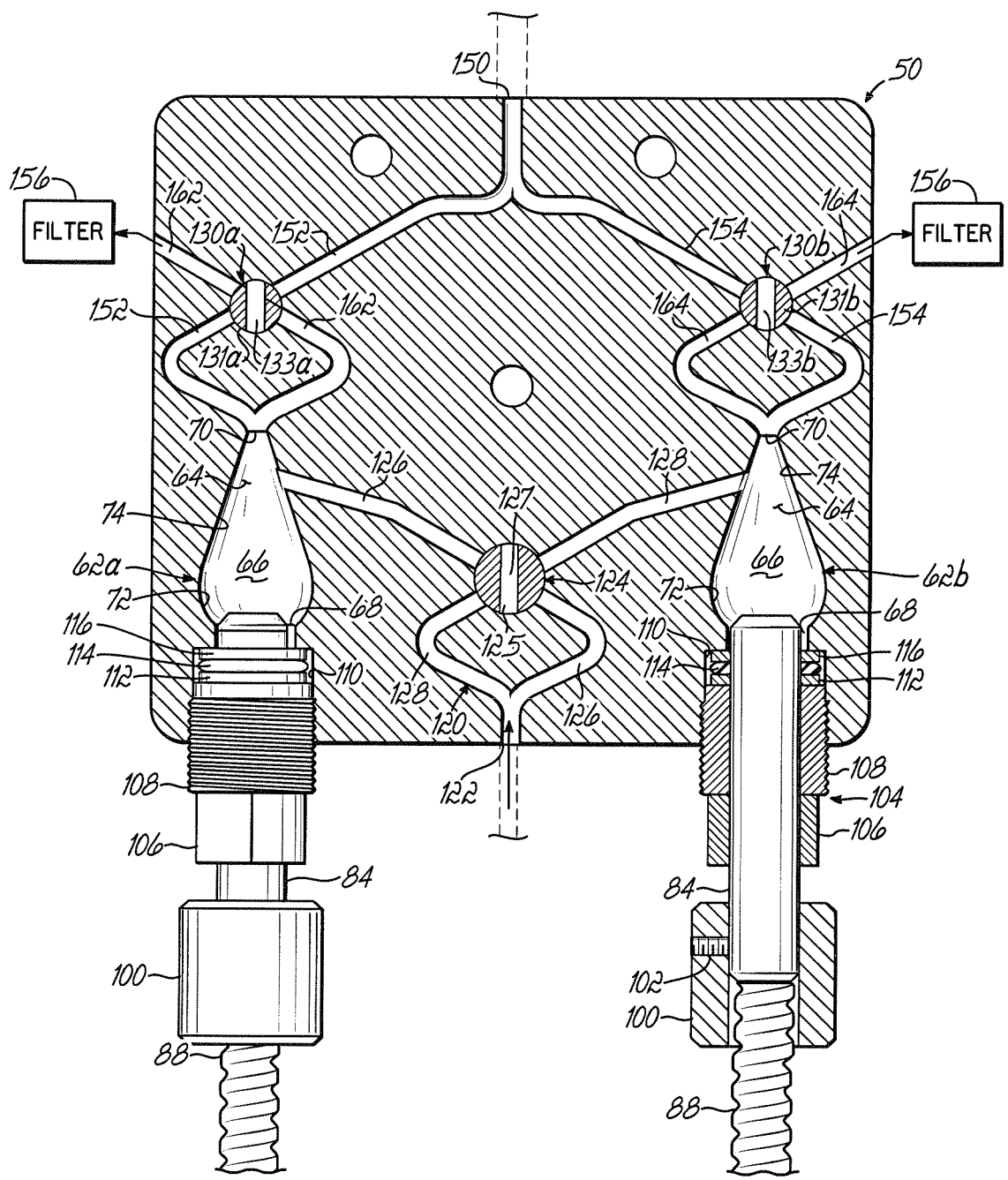
Figure 4:
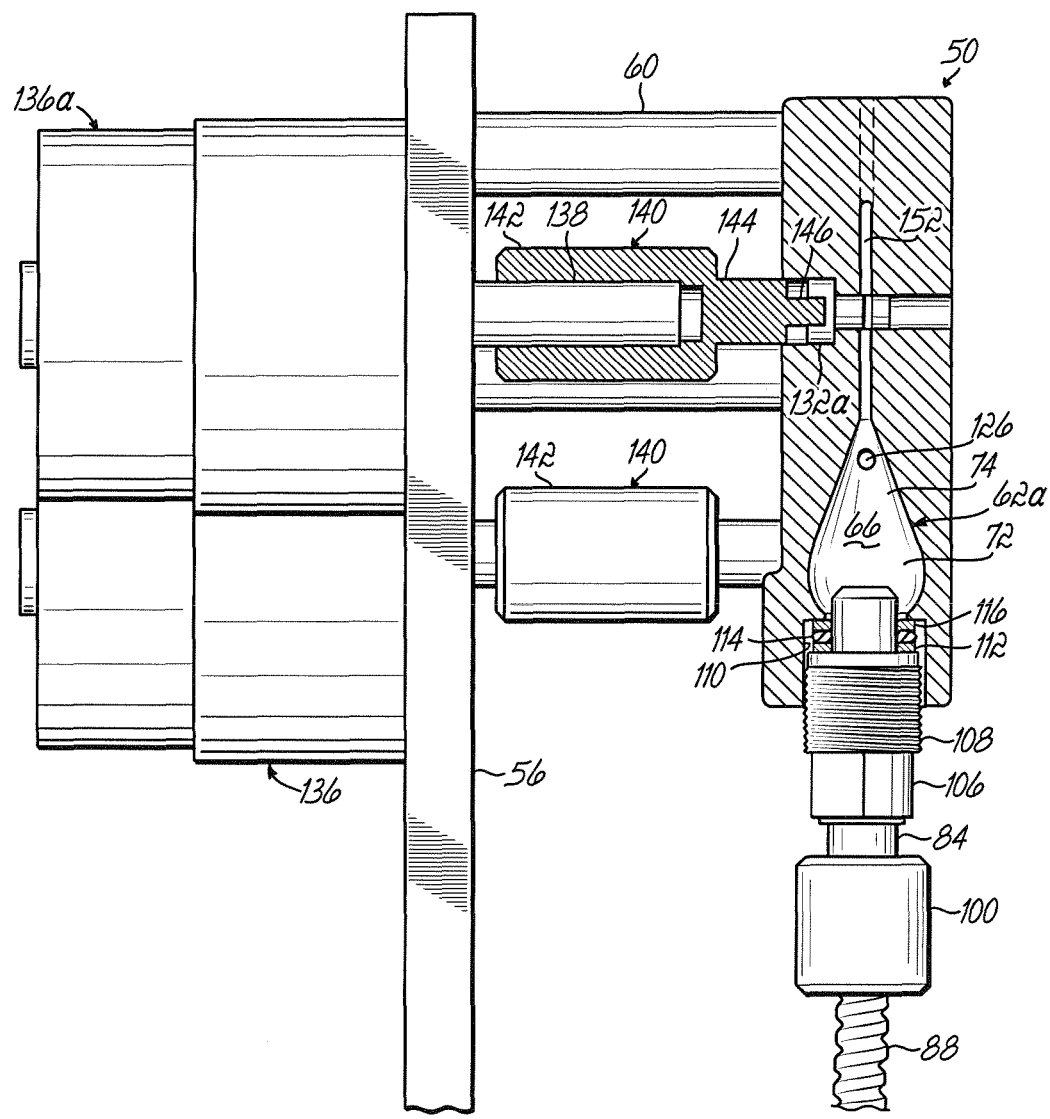
FIG. 4 is a side elevation view of the pump shown in FIGS. 2 and 3A-3C.

Referring now to FIGS. 2-4, the pump 12 shown schematically in FIG. 1 is illustrated. Pump 12 is a displacement pump and includes a pump body 50 that is adapted to be mounted to a stationary structure, such as structure 52 illustrated in FIGS. 2 and 4. In the illustrated embodiment, structure 52 includes a base plate 54 and a vertically extending member 56, extending upwardly from the base plate 54. However, the pump body 50 can be mounted to a wide variety of stationary structures having other configurations. In the illustrated embodiment, the pump body 50 is secured to the vertically extending member 56 by a plurality of conventional fasteners, such as bolts 58 that extend through sleeves 60 and into or through plate 56. The bolts 58 can be threaded into threaded holes (not shown) formed in member 56 or alternatively can pass through clearance holes in member 56 and secured by conventional fasteners such as nuts (not shown) on an opposite side of member 56. However, body 50 can be mounted to the structure 52 in any other suitable manner.

Pump body 50 is made of a non-compliant material. Examples of suitable materials include various plastics such as an acrylic material or various polycarbonates. Pump 12 further includes first 62a and second 62b pump chambers formed within the non-compliant pump body 50. Pump chambers 62a and 62b can be formed by injection molding or other suitable manufacturing processes. Each of the pump chambers 62a, 62b is defined by an interior surface 64 formed in pump body 50, and each of the chambers 62a, 62b is suitable for receiving fluid as subsequently discussed. A pair of chamber inlets 68 can be formed in pump body 50, with each disposed at one end of one of the chambers 62a, 62b. A pair of chamber outlets can be formed in pump body 50, with each being disposed at an opposite end of one of the chambers 62a, 62b, with fluid discharging therefrom as subsequently discussed.

Pump chambers 62a and 62b each include a first portion 72 that can have a generally spherical segment shape as shown in the illustrated embodiment, and disposed proximate inlet 68 and in fluid communication with the inlet 68. Each of the pump chambers 62a and 62b further include a second portion 74, integral with the first portion 72 and extending away from the first portion 72. The second portion 74 can have a conical shape as shown in the illustrated embodiment. The portion 74 of each of the pump chambers 62a and 62b converges to the corresponding outlet 70. Stated differently, the second portion 74 diverges away from the corresponding outlet 70. Due to the combination of the shape of portions 72 and 74, each of the chambers 62a and 62b are generally teardrop shaped in the illustrated embodiment. Pump chambers 62a and 62b are shaped as shown to prevent any air bubbles that may be entrained within the fluid in the interior cavities 66, from being trapped within the cavities 66. Instead, as a result of the shape of pump chambers 62a and 62b, any such air bubbles will rise upwardly through the cavities 66 and discharge through the corresponding outlet 70.

While pump chambers 62a and 62b are identically shaped and each are generally teardrop shaped in the illustrated embodiment, it is conceivable and within the scope of the present invention that pump chambers 62a and 62b can have shapes other than that shown and they can have shapes that are not identical to one another, provided that the shapes of chambers 62a and 62b prevent air bubbles from being trapped within cavities 66. When pump body 50 is mounted to the stationary structure 52, the first portion 72 of pump chambers 62a and 62b is disposed below the second portion 74 of the corresponding one of pump chambers 62a and 62b so that any air bubbles entrained within the fluid within cavities 66 rise upwardly through cavities 66 to the corresponding outlet 70.

Pump 12 further includes a pair of fluid displacement devices, indicated at 80a and 80b in FIG. 2. The fluid displacement devices 80a, 80b are mechanically coupled to pump body 50 and are operably extendable into one of the pump chambers 62a and 62b, wherein fluid is displaced out of the corresponding one of chambers 62a, 62b. Additionally, the fluid displacement devices 80a, 80b are disposed in sealing engagement with the pump body 50, as subsequently discussed.

Each of the fluid displacement devices 80a, 80b includes a linear actuator 82 and a displacement member 84 in contacting engagement with actuator 82, with each displacement member 84 mechanically coupled to pump body 50. Displacement member 84 of the actuating device 80a is extendable into the pump chamber 62a, for the purpose of displacing fluid from chamber 62a, and is disposed in sealing engagement with pump body 50. Similarly, the displacement member 84 of the actuating device 80b is extendable into the pump chamber 62b, and is also disposed in sealing engagement with the pump body 50. In the illustrated embodiment each displacement member 84 is a piston. However, displacement members 84 can be other devices and can have other shapes and sizes than the illustrated pistons. As shown in FIGS. 3A-3G, each of the displacement members 84 is spaced apart from interior surface 64 when extended into the corresponding one of pump chambers 62a and 62b.

Each of the linear actuators 82 can be a stepper motor 86 having a linearly translatable output screw 88 that is disposed in contacting engagement with the corresponding displacement member 84 during operation of pump 12. Alternatively, the linear actuators 82 can comprise devices other than stepper motors, including but not limited to pneumatically or hydraulically actuated cylinders and the like.

In the illustrated embodiment, each stepper motor 86 is secured to a plate 90 that is integral with the vertically extending member 56 of stationary structure 52 and extends horizontally away from member 56. The motors 86 can be secured to plate 90 by any conventional means, such as conventional fasteners (not shown). Plate 90 includes a pair of holes 92, suitable for receiving the output screws 88 therethrough.

Each of the actuating devices 80a, 80b further includes a coupling 100 that is secured to a corresponding displacement member 84. In the illustrated embodiment, this is accomplished by passing a setscrew (not shown) through a hole 102 formed in coupling 100, until the setscrew is disposed in contacting engagement with the displacement member 84. As best shown in FIGS. 3A-3H, the output screw 88 of each of the linear actuators 82 passes through a lower end of coupling 100 and is disposed in contacting engagement with the displacement member 84. Accordingly, as the output screw 88 is translated up or down, during operation of the linear actuator 82, the displacement member 84 moves up or down with the output screw 88. As best shown in FIGS. 3A-3H, each displacement member 84 passes through a stuffing nut 104, through the inlet 68 and into the corresponding one of the pump chambers 62a, 62b. Each stuffing nut 104 can include a lower torquing nut 106, that may have a hexagonal shape or other shape suitable for accepting a torquing device, and an upper, externally threaded barrel 108 that is integral with the torquing nut 106.

The displacement member 84 of each actuating device 82 is disposed in sealing engagement with the pump body 50 of pump 12, that can be accomplished as follows as shown in the illustrated embodiment. Pump body 50 can include a pair of recesses 110 formed therein, with each including a lower portion having internal threads that are suitable for receiving the external threads of one of the barrels 108. A lower spacer 112, such as a washer, can be disposed in contacting engagement with an upper surface of the barrel 108. A resilient member 114, such as an O-ring, can be disposed between the lower spacer 112 and an upper spacer 116, such as a washer. Displacement member 84 passes through lower spacer 112, resilient member 114 and upper spacer 116 into interior cavity 66. Each stuffing nut 104 can be torqued in a direction that causes the threaded barrel 108 to move upward within the corresponding recess 110 and force the upper washer 116 against an upper surface of recess 110. The resilient member 114 is compressed and forced radially outwardly against an inner surface of the recess 110 and radially inwardly against an outer surface of displacement member 84, thereby sealing the displacement member 84 to pump body 50, which prevents any fluid contained within the corresponding one of pump chambers 62a, 62b from escaping through inlet 68 into recess 110 and out of pump body 50. Pump 12 can further include a pair of boots (not shown), or covers, and each can extend from coupling 100 to barrel 108 for the purpose of further isolating (in addition to enclosure 14) displacement members 84 from any contamination.

Pump 12 further includes a fluid flow network, indicated generally at 120 in FIGS. 3A-3H, that is formed in the pump body 50 and is operable for supplying fluid from a source of fluid, such as the IV bag 20 shown in FIG. 1, to the pump chambers 62a, 62b, and for dispensing the fluid from the chambers 62a, 62b out of the pump body 50 during operation of pump 12. Flow network 120 can be formed in body 50 by injection molding. In the illustrated embodiment, the fluid flow network 120 includes an inlet port 122, a three position input valve 124 and first 126 and second 128 fluid supply passages that extend between the inlet port 122 and the pump chambers 62a and 62b, respectively. The fluid flow network 120 can further include a pair of three position output valves 130a, 130b positioned within the fluid flow network 120 as subsequently discussed. Input valve 124 and each of the output valves 130a, 130b are non-displacement valves. The use of non-displacement valves helps maintain the desired flow constancy of pump 12.

In the illustrated embodiment, valves 124, 130a and 130b are rotatable valves, each having a stem and a flow passage. More particularly, the input valve 124 has a stem 125 and a flow passage 127 that extends substantially straight and transversely through the stem 125. Output valve 130a can have a stem 131a and a flow passage 133a that extends substantially straight and transversely through stem 131a. Output valve 130b can have a stem 131b and a flow passage 133b that extends substantially straight and transversely through stem 131b. Additionally, each of the valves 124, 130a and 130b include a coupling portion, such as the coupling portion 132a of valve 130a shown in FIG. 4, that is integral with the stem of the corresponding valve, such as stem 131a of valve 130a. Each of the valves 124, 130a and 130b are coupled to a rotational actuator 136 shown in FIGS. 2 and 4. During operation of pump 12, the rotational actuators 136 are effective for rotating valves 124 and 130a, 130b between first, second and third positions, as subsequently discussed further. In the illustrated embodiment, each of the rotational actuators 136 is a stepper motor and is electrically coupled to a controller, such as controller 16, as shown schematically in FIG. 6. However other suitable rotational actuators may be used within the scope of the present invention. For example, solenoid operated valves can be used in lieu of the stepper motors, or any other device can be used that is suitable for rotating valves 124, 130a and 130b between their three positions. Each of the rotational actuators 136 can be mounted to a stationary structure such as member 56 of structure 52 as shown in FIGS. 2 and 4, using conventional fasteners (not shown) or other suitable means.

The manner in which the rotational actuators 136 are coupled to valve 124 and output valves 130a, 130b in the illustrated embodiment can be further understood with reference to the coupling of the rotational actuator 136a to coupling 132a of valve 130a, as shown in FIG. 4. Each of the rotational actuators 136 includes a rotatable output shaft 138 coupled to one of the valves 124, 130a and 130b. In the illustrated embodiment, a coupling member 140 is used to couple each rotatable output shaft 138 to the corresponding one of valves 124, 130a and 130b. As shown in FIG. 4, each of the coupling members 140 includes a hollow barrel 142 that is disposed in surrounding relationship with the output shaft 138. The barrels 142 can be secured to the corresponding output shaft 138 by one or more setscrews (not shown). Each coupling member 140 can further include a protruding portion 144 that is integral with the barrel 138 at one end thereof and has an opposite end 146 that can engage the coupling portion 132 of the corresponding valve, such as coupling portion 132a of valve 130a. End portion 146 can have a smaller size relative to the remainder of the protruding portion 144 and can engage the coupling portion 132 of the corresponding valve in a bayonet-type engagement, such as that shown with regard to coupling portion 132a of valve 130a in FIG. 4. Coupling portion 132a and end portion 146 of the protruding portion 144 of coupling member 140 can have flat mating surfaces to facilitate torque transfer from the output shaft 138 of rotational actuator 136, through the coupling member 140 and to the corresponding one of valves 124, 130a and 130b.

Valve 124 can be rotated by the corresponding rotational actuator 136 between: a first position shown in FIG. 3A wherein the pump chamber 62a is in fluid communication with inlet port 122; a second position shown in FIG. 3E wherein the pump chamber 62b is in fluid communication with inlet port 122; and a third position shown in FIGS. 3B, 3C, 3D, 3F, 3G and 3H wherein both of the pump chambers 62a and 62b are fluidicly uncoupled from inlet port 122. The various positions of output valves 130a, 130b are subsequently discussed.

Figure 5:
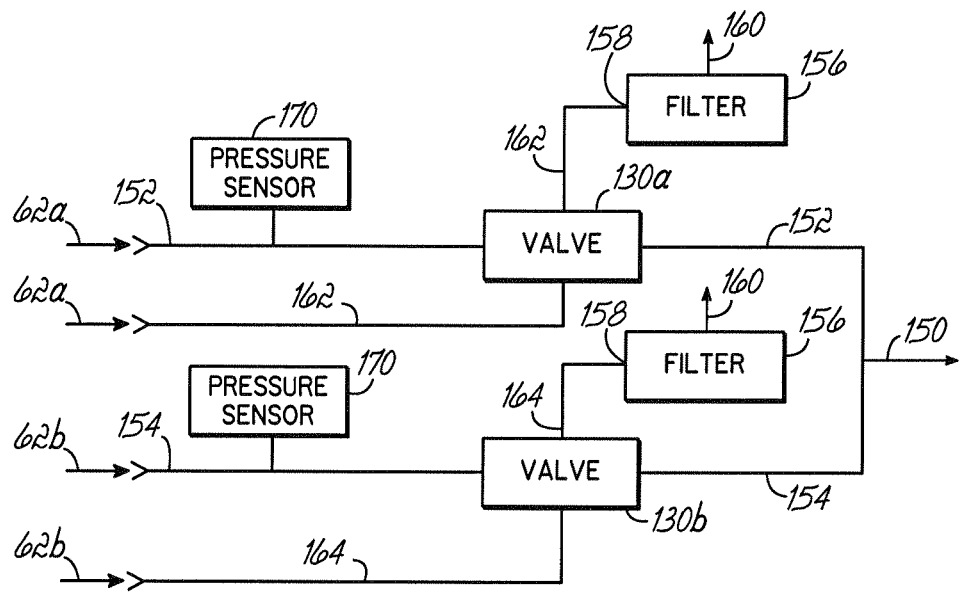
FIG. 5 is a schematic representation of air filters and pressure sensors that can be included in the pump.

Referring to FIG. 5, fluid flow network 120 further includes an outlet port 150 and fluid discharge passages 152, 154. The fluid discharge passage 152 extends between the outlet 70 that communicates with pump chamber 62a and outlet port 150 and the fluid discharge passage 154 extends between the outlet 70 that communicates with pump chamber 62b and outlet port 150. The fluid flow network 120 can also include a pair of porous air filters 156, with each selectively in fluid communication with the one of the pump chambers 62a, 62b as subsequently discussed. Filters 156 can be disposed within pump body 50 or can be positioned exterior of pump body 50. Each filter 156 includes a fluid inlet 158 and an air vent 160. Each filter 156 can include a hydrophobic medium (not shown) that repels any fluid entering filter 156 through inlet 158, but allows any air entrained within the fluid to pass therethrough and discharge from filter 156 through air vent 160. The fluid flow network 120 can include a first filter supply passage 162 that extends between the chamber outlet 70 that communicates with one of the filters 156 and a second filter supply passage 164 that extends between the chamber outlet 70 that communicates with pump chamber 62b and the other filter 156.

Output valve 130a can be rotated by the corresponding rotational actuator 136 between: a first position shown in FIGS. 3D, 3F and 3G wherein pump chamber 62a is in fluid communication with the outlet port 150; a second position shown in FIG. 3C wherein the pump chamber 62a is in fluid communication with one of the filters 156; and a third position shown in FIGS. 3A, 3B and 3H wherein pump chamber 62a is fluidicly uncoupled with outlet port 150 and filter 156. Similarly, output valve 130b can be rotated by the corresponding rotational actuator 136 between: a first position shown in FIGS. 3A-3D wherein the pump chamber 62b is in fluid communication with outlet port 150; a second position shown in FIG. 3G wherein the pump chamber 62b is in fluid communication with the other filter 156; and a third position shown in FIGS. 3E, 3F and 3H wherein the pump chamber 62b is fluidicly uncoupled with outlet port 150 and filter 156.

Pump 12 can also include a pair of pressure sensors 170, which can be pressure transducers. Each of the sensors 170 are always in fluid communication with one of the pump chambers 62a, 62b. In the illustrated FIG. 5 embodiment, one of the pressure sensors 170 is in fluid communication with the fluid discharge passage 152 at a location downstream of chamber 62a and upstream of output valve 130a. Alternatively, this sensor 170 can be disposed within the chamber 62a and can be secured to the interior surface 64, or can be positioned elsewhere provided it is always in fluid communication with chamber 62a. Similarly, in the illustrated embodiment, the other sensor 170 is in fluid communication with the fluid discharge passage 154 at a location downstream of chamber 62b and upstream of output valve 130b. Alternatively, this sensor 170 can be disposed within chamber 62b and can be secured to the interior surface 64, or can be positioned elsewhere provided it is always in fluid communication with chamber 62b.

Hospital procedures associated with infection control typically require the replacement of the portions of fluid dispensing systems that are exposed to the fluid after a relatively short, predetermined time. The components of medical fluid dispensing systems that are exposed to, or wetted by, the fluid being dispensed include the fluid supply and discharge tubing and the portions of the pump that are exposed to the medical fluid. Due to the requirement of replacing these components after a relatively short period of time, there is a requirement for providing a pump module that can be replaced easily and in a cost effective manner. The present invention provides such as a pump module that can include the following components in the illustrated embodiment: pump body 50 and the included pump chambers 62a and 62b, as well as the fluid flow network 120 that includes the non-displacement, rotational input valve 124 and the non-displacement, rotational output valves 130a and 130b; displacement members 84 and the associated stuffing nuts 104, as well as the spacers 112 and 116 and the resilient member 114; filters 156 and pressure sensors 170. Stuffing nuts 104 and spacers 112 are included in the pump module even though they may not be exposed to the fluid within chambers 62a, 62b. The remaining components of pump 12 are not exposed to the fluid being pumped, and are therefore not included in the pump module. In the embodiment where the pump body 50 is made of a plastic material, the pump module is particularly cost effective.

Figure 6:
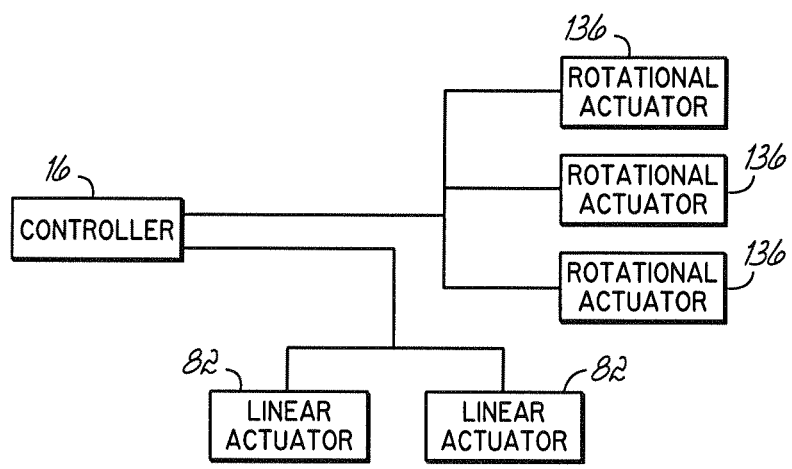
FIG. 6 is a schematic representation of a control system that can be incorporated in the pump shown in FIGS. 2, 3A-3H and 4.

The operation of pump 12 can be further understood with reference to FIGS. 1, 3A-3H and 6. As shown in FIG. 6, controller 16 controls the operation of the two linear actuators 82 and the three rotational actuators 136. Controller 16 can be programmed to operate these actuators to achieve the desired pumping cycles. The linear actuators 82 are operated independently of one another and the rotational actuators 136 are operated independently of one another. This permits fluid to be pumped out of either one of the pump chambers 62a, 62b separately and also permits fluid to be pumped out of both of the pump chambers simultaneously as required to maintain a constancy of fluid flow discharging through outlet port 150.

During the initial phase, or cycle, of operation of pump 12, one of the pump chambers 62a, 62b is filled with the fluid to be dispensed, while fluid is pumped out of the other one of pump chambers 62a, 62b and through the outlet 150 into a tubing section such as tubing section 30 shown in FIG. 1, and then to a patient. FIG. 3A illustrates this phase of operation as follows.

In FIG. 3A, the input valve 124 is shown in the position wherein pump chamber 62a is in fluid communication with the inlet 122 of the fluid flow network 120. Accordingly, fluid is supplied from a source of fluid, such as the IV bag 20 shown in FIG. 1, to pump chamber 62a. During this time, the output valve 130a is in the position wherein chamber 62a is fluidicly uncoupled with outlet port 150 and filter 156, as shown in FIG. 3A. If the pressure sensor 170 in fluid communication with pump chamber 62a records a reduction in pressure when input valve 124 is selected so that inlet 122 is in fluid communication with pump chamber 62a, a flow passage occlusion is indicated at a location upstream of input valve 124. If this occurs, pump 12 can be shut down so that the operator can investigate the source of the problem.

Fluid is pumped out of pump chamber 62b and out of the pump body 50 through outlet 150 during the time chamber 62a is being filled. This is accomplished by rotating valve 130b to the position wherein chamber 62b is in fluid communication with outlet port 150, as shown in FIG. 3A, and translating the displacement member 84 into pump chamber 62b. As noted previously, the displacement members 84 are spaced apart from the interior surfaces 64 of the corresponding pump chambers 62a, 62b. It is not necessary for the displacement members to expel all of the fluid within the corresponding chamber 62a, 62b. Instead, the amount of fluid to be displaced or pumped, is equal to the volume of the portion of the displacement member 84 that is translated into the corresponding chamber 62a, 62b. If a pressure spike, or sharp increase in pressure, occurs when output valve 130b is rotated to the foregoing position, the operator of pump 12 is alerted that there is a flow passage occlusion downstream of output valve 130*b*. The operator can then shutdown pump 12 and investigate the source of the problem.

After pump chamber 62*a* has been filled, and prior to the completion of pumping fluid out of pump chamber 62*b*, a test can be conducted to determine if any air is entrained within the fluid contained within pump chamber 62*a*. This test can be conducted as follows, with reference to FIG. 3B. Output valves 130*a* and 130*b* remain in the same position but input valve 124 is rotated to the position where the inlet port 122 is fluidicly uncoupled from both of the chambers 62*a*, 62*b* as shown in FIG. 3B. Controller 16 signals the linear actuator 82 associated with pump chamber 62*a* to translate the displacement member 84. A lack of movement of displacement member 84 coupled with a pressure increase recorded by the corresponding pressure sensor 170 indicates that air is not entrained within the fluid contained within chamber 62*a*. However, if the displacement member 84 does move, the presence of air entrained within the fluid is indicated regardless of whether the corresponding pressure sensor 164 indicates an increase or decrease in pressure. A linear encoder (not shown) can be coupled to the corresponding linear actuator 82 and can be used to measure the translation of displacement member 84.

If the foregoing test indicates the presence of air entrained within the fluid, valve 130*a* is rotated so that pump chamber 62*a* is in fluid communication with one of the filters 156 as shown in FIGS. 3C and 5. Output valve 130*b* and input valve 124 remain in the same position, as shown in FIG. 3C. Accordingly, output valve 130*b* is in fluid communication with outlet port 150 but is fluidicly uncoupled from filter 156, and input valve 124 is fluidicly uncoupled with both of the chambers 62*a*, 62*b*. Displacement member 84 is then translated into pump chamber 62*a*, which forces fluid into the associated filter 156 through inlet 158. The hydrophobic medium within filter 156 repels the fluid entering filter 156 but air within the fluid can pass through the hydrophobic medium and discharge from filter 156, through air vent 162. The foregoing test is repeated until it is determined that no air is entrained within chamber 62*a*.

After the completion of the foregoing test to determine any presence of air within the fluid within chamber 62*a*, as well as the air removal process if air is detected, the output valve 130*a* is rotated to the position wherein chamber 62*a* is in fluid communication with outlet port 150 as shown in FIG. 3D, so that fluid can be pumped out of chambers 62*a*, 62*b* simultaneously. Fluid is pumped out of chamber 62*a* by translating the associated displacement member 84 into chamber 62*a*. This simultaneous pumping out of both of the chambers 62*a* and 62*b* continues for a relatively short period of time, but ensures a constancy of flow of the fluid through outlet 150, due to the prevention of any "dead time" where no fluid is being pumped. If the pressure sensor 170 associated with chamber 62*a* records a pressure increase when valve 130*a* is opened, a flow passage occlusion downstream of valve 130*a* is indicated and pump 12 can be shutdown for the operator to investigate the source of the problem.

When the displacement member 84 associated with pump chamber 62*b* has reached the end of its stroke, or translation, output valve 130*b* is rotated to the position wherein chamber 62*b* is fluidicly uncoupled with outlet port 150 and the associated filter 156, input valve 124 is rotated to the position wherein chamber 62*b* is fluidicly coupled with inlet port 122, and output valve 130*a* remains in the same position so that chamber 62*a* remains in fluid communication with outlet port 150, with the positions of these valves illustrated in FIG. 3E. Displacement member 84 is retracted and chamber 62*b* is refilled with fluid by an amount equal to the volume of the portion of displacement member 84 retracted from interior cavity 66.

Prior to the completion of pumping fluid out of pump chamber 62*a*, a pressure test is conducted to determine if any air is present within the fluid contained in pump chamber 62*b*, in the same manner as discussed with respect to pump chamber 62*a*. The positions of input valve 124 and output valves 130*a*, 130*b* during this test are illustrated in FIG. 3F. If air is detected, output valve 62*b* is rotated so chamber 62*b* is in fluid communication with the associated filter 156 and the air can be removed as discussed previously with respect to pump chamber 62*a*. The positions of input valve 124 and output valves 130*a*, 130*b* during this air removal process are illustrated in FIG. 3G.

After the completion of the foregoing test to determine any presence of air within the fluid contained within chamber 62*b*, as well as the air removal process if required, the output valve 130*b* is opened and the displacement member 84 associated with pump chamber 62*b* is translated into pump chamber 62*b* so that fluid is pumped out of chambers 62*a* and 62*b* simultaneously for a relatively short period of time to ensure constancy of flow of the fluid through outlet 150, due to the prevention of any "dead time" where no fluid is being pumped.

Pumping is continued, with fluid alternately pumped out of pump chambers 62*a*, 62*b* until the desired quantity of medical fluid has been supplied to the patient. At that time, pump 12 is shutdown and output valves 130*a*, 130*b* are rotated to the positions shown in FIG. 3H wherein each pump chamber 62*b*, 62*b* is fluidicly uncoupled with outlet port 150 and the associated filter 156. The input valve 124 remains in the same position wherein each chamber 62*a*, 62*b* is fluidicly uncoupled with inlet port 122, as shown in FIG. 3H.

While the foregoing description has set forth various embodiments of the present invention in particular detail, it must be understood that numerous modifications, substitutions and changes can be undertaken without departing from the true spirit and scope of the present invention as defined by the ensuing claims. For example, while the fluid flow network of the illustrated embodiment includes a single, three position input valve and a pair of three position output valves, fluid flow networks according to the principles of the present invention can incorporate different numbers of valves and the valves can have different configurations, i.e., they may not be three position valves. Also, while a pair of porous air filters are included in the illustrated embodiment for the purpose of removing any air bubbles in the fluid being pumped to a patient, any such air bubbles can be removed by a single filter, with appropriate fluid passages within the fluid flow network, or by manually priming the pump, without using an air filter. Pumps in accordance with the principles of the present invention can be used in a variety of applications, ranging from low to high volume fluid applications. However, pumps in accordance with the principles of the present invention have particularly advantageous use in large volume fluid applications. The invention is therefore not limited to specific embodiments as described, but is only limited as defined by the following claims.

What is claimed is:

1. A pump module for use in a medical fluid dispensing system comprising:
　a pump body;
　first and second pump chambers, each having an interior bounded by an interior surface of the pump body and defining a predetermined interior shape of the pump chamber;

first and second fluid supply passages coupled into fluid communication with the interior of the corresponding first and second pump chambers;

first and second chamber outlets associated with the corresponding first and second pump chambers, each chamber outlet coupled to the interior surface and in fluid communication with the interior of the corresponding pump chamber, such that each of the first and second pump chambers acts as a fluid reservoir between the corresponding fluid supply passage and the corresponding chamber outlet; and first and second chamber inlets associated with the corresponding first and second pump chambers, each chamber inlet coupled to the interior surface and in fluid communication with the interior of the corresponding pump chamber, each of the first and second chamber inlets configured to receive a displacement member therethrough into the interior of the corresponding pump chamber such that movement of the displacement member relative to the interior surface causes fluid to move between the fluid supply passage and the chamber outlet through the pump chamber;

wherein the predetermined interior shape of each of the pump chambers comprises a first portion having a generally spherical segment shape and a second portion integral with the first portion and having a generally conical shape, the first and second portions being in fluid communication with the chamber inlet and the chamber outlet;

the second, generally conically shaped portion of each of the pump chambers converges to the corresponding chamber outlet.

2. A pump module as recited in claim 1, wherein:
the pump body is made of a non-compliant material.

3. A pump module as recited in claim 1, further comprising:
a fluid flow network formed in the pump body and operable for supplying fluid from a source of fluid to the first and second fluid supply passages and the first and second pump chambers and for dispensing fluid from the first and second pump chambers out of the pump body during operation of the pump module.

4. A pump module as recited in claim 3, wherein:
the fluid flow network comprises a plurality of non-displacement valves.

5. A pump module as recited in claim 4, wherein:
each of the non-displacement valves is a rotatable valve comprising a stem defining an axis of rotation, a coupling portion integral with the stem and a flow passage;
the flow passage of each of the valves extends substantially straight through the stem and transverse to the axis of rotation; and
the coupling portion is adapted to be coupled to a rotational actuator.

6. A pump module as recited in claim 4, wherein:
a first one of the non-displacement valves is a three position input valve; the pump module further comprising:
an inlet port;
the first fluid supply passage being in fluid communication with the inlet port and the first pump chamber when the input valve is in a first position;
the second fluid supply passage being in fluid communication with the inlet port and the second pump chamber when the input valve is in a second position; and
the first pump chamber and the second pump chamber are fluidicly uncoupled with the inlet port when the input valve is in a third position.

7. A pump module as recited in claim 6, wherein the fluid flow network further comprises:
an outlet port;
a first fluid discharge passage disposed between and in fluid communication with the first chamber outlet and the outlet port;
a second fluid discharge passage disposed between and in fluid communication with the second chamber outlet and the outlet port; wherein
a second one of the non-displacement valves is a first output valve disposed in the first fluid discharge passage;
a third one of the non-displacement valves is a second output valve disposed in the second fluid discharge passage;
the pump module further comprises a pair of porous air filters, each being selectively in fluid communication with one of the pump chambers;
the outlet port is in fluid communication with the first pump chamber when the first output valve is in a first position, the first pump chamber is in fluid communication with one of the filters when the first output valve is in a second position, and the first pump chamber and the outlet port are fluidicly uncoupled when the first output valve is in a third position;
the outlet port is in fluid communication with the second pump chamber when the second output valve is in a first position, the second pump chamber is in fluid communication with the other one of the filters when the second output valve is in a second position, and the second pump chamber and the outlet port are fluidicly uncoupled when the second output valve is in a third position.

8. A pump module as recited in claim 3, further comprising:
a first fluid displacement member mechanically coupled to the pump body and operably extendable into the interior of the first pump chamber, wherein fluid is displaced out of the first pump chamber into the fluid flow network; and
a second fluid displacement member mechanically coupled to the pump body and operably extendable into the interior of the second pump chamber, wherein fluid is displaced out of the second pump chamber into the fluid flow network.

9. A pump module as recited in claim 1, further comprising:
a pair of porous air filters, each having a fluid inlet and an air vent; wherein
the fluid inlet of each of the air filters is selectively in fluid communication with one of the pump chambers; and
each of the porous air filters is operably effective for filtering air entrained within a fluid supplied to the fluid inlet of the filter and discharging the air through the air vent.

10. A pump module as recited in claim 9, wherein:
each of the porous air filters comprises a hydrophobic medium.

11. A pump module as recited in claim 10, wherein:
each of the porous air filters comprises a Gortex® air filter.

12. A pump module as recited in claim 1, further comprising:
a pair of pressure sensors, each of the pressure sensors being in fluid communication with one of the pump chambers.

13. A pump module as recited in claim 1, wherein:
the pump body is made of a plastic material.

14. A pump module for use in a medical fluid dispensing system comprising:
a pump body;

first and second pump chambers, each having an interior bounded by an interior surface of the pump body and defining a predetermined interior shape of the pump chamber;

first and second fluid supply passages coupled into fluid communication with the interior of the corresponding first and second pump chambers;

first and second chamber outlets associated with the corresponding first and second pump chambers, each chamber outlet coupled to the interior surface and in fluid communication with the interior of the corresponding pump chamber, such that each of the first and second pump chambers acts as a fluid reservoir between the corresponding fluid supply passage and the corresponding chamber outlet; and first and second chamber inlets associated with the corresponding first and second pump chambers, each chamber inlet coupled to the interior surface and in fluid communication with the interior of the corresponding pump chamber, each of the first and second chamber inlets configured to receive a displacement member therethrough into the interior of the corresponding pump chamber such that movement of the displacement member relative to the interior surface causes fluid to move between the fluid supply passage and the chamber outlet through the pump chamber; wherein at least a portion of the pump chamber converges to the corresponding chamber outlet, for each of the pump chambers.

15. A pump module as recited in claim 14, further comprising:

a fluid flow network formed in the pump body and operable for supplying fluid from a source of fluid to the first and second supply passages and the first and second pump chambers and out of the pump body during operation of the pump module.

16. A pump module as recited in claim 15, further comprising:

a first fluid displacement member mechanically coupled to the pump body and operably extendable into the first pump chamber, wherein fluid is displaced out of the first pump chamber into the fluid flow network; and a second fluid displacement member mechanically coupled to the pump body and operably extendable into the second pump chamber, wherein fluid is displaced out of the second pump chamber into the fluid flow network.

17. A pump module as recited in claim 14, further comprising:

a pair of porous air filters, each having a fluid inlet and an air vent; wherein the fluid inlet of each of the porous air filters is selectively in fluid communication with one of the pump chambers;

each of the porous air filters is operably effective for filtering air entrained within a fluid supplied to the fluid inlet of said filter and discharging the air through the air vent.

18. A pump module as recited in claim 17, wherein:

each of the porous air filters comprises a hydrophobic medium.

19. A pump module as recited in claim 18, wherein:

each of the porous air filters comprises a Gortex® air filter.

20. A pump module as recited in claim 14, further comprising:

a pair of pressure sensors, each of the pressure sensors being in fluid communication with one of the pump chambers.

21. A pump module as recited in claim 14, wherein:

the pump body is made of a plastic material.

22. A pump module for use in a medical fluid dispensing system comprising:

a pump body;

first and second pump chambers, each having an interior bounded by an interior surface of the pump body and defining a predetermined interior shape of the pump chamber, the predetermined interior shape being generally teardrop shaped;

first and second fluid supply passages coupled into fluid communication with the interior of the corresponding first and second pump chambers;

first and second chamber outlets associated with the corresponding first and second pump chambers, each chamber outlet coupled to the interior surface and in fluid communication with the interior of the corresponding pump chamber, such that each of the first and second pump chambers acts as a fluid reservoir between the corresponding fluid supply passage and the corresponding chamber outlet;

first and second chamber inlets associated with the corresponding first and second pump chambers, each chamber inlet coupled to the interior surface and in fluid communication with the interior of the corresponding pump chamber, each of the first and second chamber inlets configured to receive a displacement member therethrough into the interior of the corresponding pump chamber such that movement of the displacement member relative to the interior surface causes fluid to move between the fluid supply passage and the chamber outlet through the pump chamber;

a fluid flow network formed in the pump body and operable for supplying fluid from a source of fluid to the first and second fluid supply passages and the first and second pump chambers and for dispensing fluid from the pump chambers out of the pump body during operation of the pump module;

a first fluid displacement member mechanically coupled to the pump body and operably extendable into the interior of the first pump chamber, wherein fluid is displaced out of the first pump chamber into the fluid flow network; and a second fluid displacement member mechanically coupled to the pump body and operably extendable into the interior of the second pump chamber, wherein fluid is displaced out of the second pump chamber into the fluid flow network, the first and second fluid displacement members being independently operable from one another.

23. A pump module for use in a medical fluid dispensing system comprising:

a pump body made of a plastic material;

first and second pump chambers, each having an interior bounded by an interior surface of the pump body and defining a predetermined interior shape of the pump chamber;

first and second fluid supply passages coupled into fluid communication with the interior of the corresponding first and second pump chambers;

first and second chamber outlets associated with the corresponding first and second pump chambers, each chamber outlet coupled to the interior surface and in fluid communication with the interior of the corresponding pump chamber, such that each of the first and second pump chambers acts as a fluid reservoir between the corresponding fluid supply passage and the corresponding chamber outlet;

first and second chamber inlets associated with the corresponding first and second pump chambers, each chamber inlet coupled to the interior surface and in fluid communication with the interior of the corresponding pump chamber, each of the first and second chamber inlets configured to receive a displacement member therethrough into the interior of the corresponding pump chamber such that movement of the displacement member relative to the interior surface causes fluid to move between the fluid supply passage and the chamber outlet through the pump chamber; and a fluid flow network formed in the pump body and operable for supplying fluid from a source of fluid to the first and second fluid supply passages and the first and second pump chambers, and for dispensing fluid from the pump chambers out of the pump body during operation of the pump module.

24. A pump module as recited in claim 23, further comprising:

a first fluid displacement member mechanically coupled to the pump body and operably extendable into the first pump chamber, wherein fluid is displaced out of the first pump chamber into the fluid flow network; and a second fluid displacement member mechanically coupled to the pump body and operably extendable into the second pump chamber, wherein fluid is displaced out of the second pump chamber into the fluid flow network.

25. A pump module as recited in claim 23, wherein:

the fluid flow network comprises a plurality of non-displacement valves.

26. A pump module as recited in claim 25, wherein:

each of the non-displacement valves is a rotatable valve comprising a stem defining an axis of rotation, a coupling portion integral with the stem and a flow passage;

the flow passage of each of the valves extends substantially straight through the stem and transverse to the axis of rotation; and the coupling portion is adapted to be coupled to a rotational actuator.

27. A pump module as recited in claim 26, wherein:

a first one of the rotatable, non-displacement valves is a three position input valve;

a second one of the rotatable, non-displacement valves is a first output valve;

a third one of the rotatable, non-displacement valves is a second output valve;

the input valve, the first output valve and the second output valve are each adapted to be coupled to a rotational actuator.

28. A pump module for use in a medical fluid dispensing system comprising:

a pump body;

a pump chamber having an interior bounded by an interior surface of the pump body and defining a predetermined interior shape of the pump chamber;

a fluid supply passage coupled into fluid communication with the interior of the pump chamber;

a chamber outlet associated with the pump chamber, the chamber outlet coupled to the interior surface and in fluid communication with the interior of the pump chamber, such that the pump chamber acts as a fluid reservoir between the fluid supply passage and the chamber outlet;

a chamber inlet associated with the pump chamber, the chamber inlet coupled to the interior surface and in fluid communication with the interior of the pump chamber, the chamber inlet configured to receive a displacement member therethrough into the interior of the pump chamber such that movement of the displacement member relative to the interior surface causes fluid to move between the fluid supply passage and the chamber outlet through the pump chamber; wherein at least a portion of the pump chamber converges to the chamber outlet.

29. A method of manufacturing a pump module for use in a medical fluid dispensing system comprising:

using a plastic material to make a pump body of the module;

forming first and second pump chambers within the pump body, each of the first and second pump chambers having an interior bounded by an interior surface of the pump body and defining a predetermined interior shape of the pump chamber;

forming first and second fluid supply passages within the pump body, each of the fluid supply passages coupled into fluid communication with the interior of the corresponding pump chamber;

forming first and second chamber outlets within the pump body, each of the chamber outlets coupled to the interior surface and in fluid communication with the interior of the corresponding pump chamber, such that each of the first and second pump chambers acts as a fluid reservoir between the corresponding fluid supply passage and the corresponding chamber outlet;

forming first and second chamber inlets within the pump body, each of the chamber inlets coupled to the interior surface and in fluid communication with the interior of the corresponding pump chamber, each of the chamber inlets configured to receive a displacement member therethrough into the interior of the corresponding pump chamber such that movement of the displacement member relative to the interior surface causes fluid to move between the fluid supply passage and the chamber outlet through the pump chamber; and forming a fluid flow network within the pump body, wherein the fluid flow network communicates with the pump chambers.

30. A method as recited in claim 29, wherein the step of forming first and second pump chambers comprises:

forming the first and second pump chambers to have a generally teardrop shape.

31. A method as recited in claim 29, wherein the step of forming first and second pump chambers comprises:

forming each of the first and second pump chambers to comprise a first portion having a generally spherical segment shape and a second portion integral with the first portion and having a fixed, generally conical shape.

32. A method as recited in claim 29, wherein the step of forming first and second pump chambers comprises:

injection molding the first and second pump chambers.

33. A pump for use in a medical fluid dispensing system comprising:

a pump body made of a non-compliant material;

first and second pump chambers, each having an interior bounded by an interior surface of the pump body and defining a predetermined interior shape of the pump chamber;

first and second fluid supply passages coupled into fluid communication with the interior of the corresponding first and second pump chambers;

first and second chamber outlets associated with the corresponding first and second pump chambers, each chamber outlet coupled to the interior surface and in fluid communication with the interior of the corresponding pump chamber, such that each of the first and second pump chambers acts as a fluid reservoir between the corresponding fluid supply passage and the corresponding chamber outlet;

first and second chamber inlets associated with the corresponding first and second pump chambers, each chamber inlet coupled to the interior surface and in fluid communication with the interior of the corresponding pump chamber, each of the first and second chamber inlets configured to receive a displacement device therethrough into the interior of the corresponding pump chamber such that movement of the displacement device relative to the interior surface causes fluid to move between the fluid supply passage and the chamber outlet through the pump chamber;

a fluid flow network formed in the pump body and operable for supplying fluid from a source of fluid to the first and second fluid supply passages and the first and second pump chambers, and for dispensing fluid from the pump chambers out of the pump body during operation of the pump;

a first fluid displacement device mechanically coupled to the pump body and operably extendable into the interior of the first pump chamber, wherein fluid is displaced out of the first pump chamber into the fluid flow network; and a second fluid displacement device mechanically coupled to the pump body and operably extendable into the interior of the second pump chamber, wherein fluid is displaced out of the second pump chamber into the fluid flow network; wherein the first and second fluid displacement devices are operable independently from one another.

34. A pump as recited in claim 33, wherein:
at least a portion of each of the pump chambers converges to the corresponding chamber outlet.

35. A pump as recited in claim 33, wherein:
each of the pump chambers is generally teardrop shaped.

36. A pump as recited in claim 33, wherein:
each of the pump chambers further comprises a first portion having a generally spherical segment shape and a second portion integral with the first portion and having a generally conical shape, the first and second portions being disposed between the chamber inlet and the chamber outlet; and
the second, generally conically shaped portion converges to the chamber outlet.

37. A pump as recited in claim 33, wherein:
each of the first and second fluid displacement devices comprises a piston.

38. A pump as recited in claim 33, wherein:
the first and second fluid displacement devices are disposed in sealing engagement with the pump body.

39. A pump as recited in claim 33, wherein:
the first and second fluid displacement devices comprise first and second displacement members, respectively;
the first displacement member is spaced apart from the interior surface defining the first pump chamber when the first displacement member is extended into the first pump chamber; and
the second displacement member is spaced apart from the interior surface defining the second pump chamber when the second displacement member is extended into the second pump chamber.

40. A pump as recited in claim 33, wherein:
the first fluid displacement device comprises a first linear actuator and a first fluid displacement member translatable by the first linear actuator and operably extendable into the first pump chamber;
the second fluid displacement device comprises a second linear actuator and a second fluid displacement member translatable by the second linear actuator and operably extendable into the second pump chamber.

41. A pump as recited in claim 40, wherein:
the first linear actuator comprises a first stepper motor having an output screw in contacting engagement with the first fluid displacement member; and
the second linear actuator comprises a second stepper motor having an output screw in contacting engagement with the second fluid displacement member; and
the first and second output screws are linearly translatable.

42. A pump as recited in claim 40, wherein:
the first and second fluid displacement members each comprises a piston.

43. A pump as recited in claim 36, wherein:
the pump body is adapted to be mounted to a stationary structure, wherein the pump body is oriented so that the first portion of each of the pump chambers is disposed above the second portion of the corresponding one of the pump chambers during operation of the pump.

44. A pump as recited in claim 33, wherein the fluid flow network comprises:
an inlet port;
a three position input valve; wherein
the first fluid supply passage is in fluid communication with the inlet port and the first pump chamber when the input valve is in a first position;
the second fluid supply passage is in fluid communication with the inlet port and the second pump chamber when the input valve is in a second position; and
the first pump chamber and the second pump chamber are fluidicly uncoupled with the inlet port when the input valve is in a third position.

45. A pump as recited in claim 44, wherein said fluid flow network further comprises:
an outlet port;
a first fluid discharge passage disposed between and in fluid communication with the first pump chamber and the outlet port;
a second fluid discharge passage disposed between and in fluid communication with the second pump chamber and the outlet port;
a first output valve disposed in the first fluid discharge passage; and
a second output valve disposed in the second fluid discharge passage; wherein
the pump further comprises a pair of porous air filters, each being selectively in fluid communication with one of the pump chambers;
the outlet port is in fluid communication with the first pump chamber when the first output valve is in a first position, the first pump chamber is in fluid communication with one of the filters when the first output valve is in a second position, and the first pump chamber and the outlet port are fluidicly uncoupled when the first output valve is in a third position; and
the outlet port is in fluid communication with the second pump chamber when the second output valve is in a first position, the second pump chamber is in fluid communication with the other one of said filters when the second output valve is in a second position, and the second pump chamber and the outlet port are fluidicly uncoupled when the second output valve is in a third position.

46. A pump as recited in claim 45, wherein:
the input valve, the first output valve and the second output valve each comprise a non-displacement valve.

47. A pump as recited in claim 45, wherein:
the first and second output valves each comprises a rotatable valve having a stem defining an axis of rotation and a flow passage extending substantially straight through the stem and transverse to the axis of rotation;
the flow passage of the first output valve is in fluid communication with the first pump chamber and the outlet port when the first output valve is in the first position; and
the flow passage of the second output valve is in fluid communication with the second pump chamber and the outlet port when the second output valve is in the first position.

48. A pump as recited in claim 47, wherein:
the input valve comprises a rotatable valve having a stem defining an axis of rotation and a flow passage extending substantially straight through the stem and transverse to the axis of rotation, the pump further comprising:
a plurality of rotational actuators each having a rotatable output shaft; wherein
the output shaft of a first one of the rotational actuators is coupled to the input valve and is operably effective for rotating the input valve between the first, second and third positions;
the output shaft of a second one of the rotational actuators is coupled to the first output valve and is operably effective for rotating the first output valve between the first, second and third positions;
the output shaft of a third one of the rotational actuators is coupled to the second output valve and is operably effective for rotating the second output valve between the first, second and third positions.

49. A pump as recited in claim 48, wherein:
each of the rotational actuators comprises a stepper motor.

50. A pump as recited in claim 33, further comprising:
first and second pressure sensors; wherein
the first pressure sensor is in fluid communication with the first pump chamber; and
the second pressure sensor is in fluid communication with the second pump chamber.

51. A pump as recited in claim 33, further comprising:
a pair of porous air filters having a fluid inlet and an air vent; wherein
the fluid inlet of each one of the porous air filters is selectively in fluid communication with one of the pump chambers;
each of the porous air filters is operably effective for filtering air entrained within a fluid supplied to the fluid inlet of the filter and discharging the air through the air vent.

52. A pump as recited in claim 51, wherein:
each of the porous air filters comprises a hydrophobic medium.

53. A pump as recited in claim 51, wherein:
each of the porous air filters comprises a Gortex® air filter.

54. A method for pumping fluid in a medical fluid dispensing system comprising the steps of:
providing a pump comprising a pump body made of a non-compliant material, first and second pump chambers having an interior bounded by an interior surface of the pump body and defining a predetermined interior shape of the pump chamber, the pump further including first and second fluid supply passages coupled into fluid communication with the interior of the corresponding first and second pump chambers, first and second chamber outlets coupled into fluid communication with the interior of the corresponding first and second pump chambers such that the pump chambers act as fluid reservoirs between the corresponding fluid supply passage and chamber outlet, first and second chamber inlets coupled into fluid communication with the interior of the corresponding pump chamber and configured to receive a displacement member therethrough, and a fluid flow network formed in the pump body;
supplying fluid through the fluid flow network to the pump chambers;
independently pumping at least a portion of the fluid out of each of the pump chambers, through the fluid flow network and out of the pump.

55. A method as recited in claim 54, wherein the step of pumping further comprises:
initiating a first pumping cycle to pump at least a portion of the fluid out of the first pump chamber;
initiating a second pumping cycle, before the first pumping cycle is completed, to pump at least a portion of the fluid out of the second pump chamber.

56. A method as recited in claim 55, further comprising:
refilling the interior cavity of the first pump chamber after the completion of the first pumping cycle and during the second pumping cycle.

57. A method as recited in claim 56, further comprising:
testing for the presence of air within the first pump chamber after the completion of the refilling step.

58. A method as recited in claim 57, further comprising:
refilling the interior cavity of the second pump chamber after the completion of the second pumping cycle and during a third pumping cycle.

59. A method as recited in claim 58, further comprising:
testing for the presence of air within the second pump chamber after the completion of the refilling step.

60. A pump module for use in a medical fluid dispensing system comprising:
a pump body made of a plastic material;
first and second pump chambers formed in the pump body; and
a fluid flow network formed in the pump body and operable for supplying fluid from a source of fluid to the pump chambers, and for dispensing fluid from the pump chambers out of the pump body during operation of the pump module; said fluid flow network comprising a plurality of non-displacement valves,
wherein each of the non-displacement valves is a rotatable valve comprising a stem defining an axis of rotation, a coupling portion integral with the stem and a flow passage; the flow passage of each of the valves extends substantially straight through the stem and transverse to the axis of rotation; and the coupling portion is adapted to be coupled to a rotational actuator.

61. A pump module as recited in claim 60, wherein:
a first one of the rotatable, non-displacement valves is a three position input valve;
a second one of the rotatable, non-displacement valves is a first output valve;
a third one of the rotatable, non-displacement valves is a second output valve;
the input valve, the first output valve and the second output valve are each adapted to be coupled to a rotational actuator.

62. A method of manufacturing a pump module for use in a medical fluid dispensing system comprising:
using a plastic material to make a pump body of the module;

forming first and second pump chambers within the pump body, each of the first and second pump chambers having an interior cavity;

forming a fluid flow network within the pump body, wherein the fluid flow network communicates with the pump chambers; and inserting a plurality of non-displacement valves into the fluid flow network, wherein each of said non-displacement valves is a rotatable valve comprising a stem defining an axis of rotation, a coupling portion integral with the stem and a flow passage; the flow passage of each of the valves extends substantially straight through the stem and transverse to the axis of rotation; and the coupling portion is adapted to be coupled to a rotational actuator.

* * * * *

UNITED STATES PATENT AND TRADEMARK OFFICE
CERTIFICATE OF CORRECTION

PATENT NO.        : 8,876,765 B2                          Page 1 of 1
APPLICATION NO.   : 11/749265
DATED             : November 4, 2014
INVENTOR(S)       : Stanley Paul Mack et al.

It is certified that error appears in the above-identified patent and that said Letters Patent is hereby corrected as shown below:

In the Claims:

At column 18, claim 31, line 50, after "a", delete "fixed,"

Signed and Sealed this
Twenty-seventh Day of October, 2015

Michelle K. Lee
*Director of the United States Patent and Trademark Office*